(12) United States Patent
Epstein et al.

(10) Patent No.: US 8,883,497 B2
(45) Date of Patent: Nov. 11, 2014

(54) HUMAN MYELOID DERIVED SUPPRESSOR CELL CANCER MARKERS

(75) Inventors: Alan L. Epstein, Pasadena, CA (US); Melissa G. Lechner, Pasadena, CA (US)

(73) Assignee: University of Southern California, Los Angeles, CA (US)

( * ) Notice: Subject to any disclaimer, the term of this patent is extended or adjusted under 35 U.S.C. 154(b) by 0 days.

(21) Appl. No.: 13/458,788

(22) Filed: Apr. 27, 2012

(65) Prior Publication Data

US 2012/0276004 A1 Nov. 1, 2012

Related U.S. Application Data

(60) Provisional application No. 61/480,311, filed on Apr. 28, 2011, provisional application No. 61/567,042, filed on Dec. 5, 2011.

(51) Int. Cl.
  *G01N 33/50* (2006.01)
  *C12N 5/078* (2010.01)
  *G01N 33/574* (2006.01)

(52) U.S. Cl.
  CPC .......... *C12N 5/0634* (2013.01); *G01N 2800/52* (2013.01); *C12N 2502/30* (2013.01); *G01N 33/5047* (2013.01); *C12N 2503/02* (2013.01); *G01N 33/5011* (2013.01); *C12Q 2600/158* (2013.01); *G01N 33/57484* (2013.01); *C12Q 2600/106* (2013.01)
  USPC .......................................... 435/325; 435/7.23

(58) Field of Classification Search
  None
  See application file for complete search history.

(56) References Cited

U.S. PATENT DOCUMENTS

2011/0059106 A1  3/2011 Kuchroo et al.

FOREIGN PATENT DOCUMENTS

WO  WO-2010/055340 A1  5/2010
WO  WO-2010/062990 A1  6/2010

OTHER PUBLICATIONS

Lechner et al, J Immunol 185:2273-84, published only Jul. 2010, IDS filed Feb. 19, 2013.*
Diaz-Montero et al, Cancer Immunol Immunotherapy 58:49-59, 2009.*
Wincewicz et al, Folia Hitochemica Et Cytobiologica 47:435-430, 2009.*
Bronte et al (Nature reviews of Immunology, poster), 2010.*
International Search Report for PCT/US2012/035586 dated Nov. 14, 2012.
Lechner et al., "Characterization of cytokine-induced myeloid-derived suppressor cells from normal human peripheral blood mononuclear cells," The Journal of Immunology 185(4): 2273-2284 (2010).

* cited by examiner

*Primary Examiner* — Lei Yao
(74) *Attorney, Agent, or Firm* — Foley & Lardner LLP; Antoinette F. Konski

(57) ABSTRACT

Provided herein are methods for determining the presence of cancer (malignant versus benign), monitoring the progression of cancer, monitoring cancer relapse, monitoring the response to cancer therapy, or cancer staging in a subject, by evaluating $CD33^+/HLA\text{-}DR^{low}$, $CD14^+/HLA\text{-}DR^{low}$, $CD66b^+/HLA\text{-}DR^{low}$ or, $CD11b^+/HLA\text{-}DR^{low}$ MDSC for activation of a transcription factor. Transcription factors include, but are not limited to, STAT3, pSTAT3, HIF1α, or C/EBPβ. The MDSC phenotype can be $CD33^+HLA\text{-}DR^{low}HIF1\alpha^+/STAT3^+$, $CD14^+HLA\text{-}DR^{low}HIF1\alpha^+/STAT3^+/pSTAT3^+/C/EBPb^+$, $CD66b^+HLA\text{-}DR^{low}HIF1\alpha^+/STAT3^+/pSTAT3^+/C/EBPb^+$, $CD33^+HLA\text{-}DR^{low}HIF1\alpha^+/STAT3^+/pSTAT3^+/C/EBPb^+$, $CD11b^+HLA\text{-}DR^{low}HIF1\alpha^+/STAT3^+/pSTAT3^+/C/EBPb^+$, or $CD11b^+HLA\text{-}DR^{low}C/EBP\beta^+$. Also provided herein are methods for inducing human MDSC from healthy donor peripheral blood mononuclear cells (PBMC) by co-culturing PBMC with human solid tumor cell lines and subsequently measuring their suppressive ability.

8 Claims, 18 Drawing Sheets

```
  10         20         30         40         50         60
MAQWNQLQQL DTRYLEQLHQ LYSDSFPMEL RQFLAPWIES QDWAYAASKE SHATLVFHNL
  70         80         90        100        110        120
LGEIDQQYSR FLQESNVLYQ HNLRRIKQFL QSRYLEKPME IARIVARCLW EESRLLQTAA
 130        140        150        160        170        180
TAAQQGGQAN HPTAAVVTEK QQMLEQHLQD VRKRVQDLEQ KMKVVENLQD DFDFNYKTLK
 190        200        210        220        230        240
SQGDMQDLNG NNQSVTRQKM QQLEQMLTAL DQMRRSIVSE LAGLLSAMEY VQKTLTDEEL
 250        260        270        280        290        300
ADWKRRQQIA CIGGPPNICL DRLENWITSL AESQLQTRQQ IKKLEELQQK VSYKGDPIVQ
 310        320        330        340        350        360
HRPMLEERIV ELFRNLMKSA FVVERQPCMP MHPDRPLVIK TGVQFTTKVR LLVKFPELNY
 370        380        390        400        410        420
QLKIKVCIDK DSGDVAALRG SRKFNILGTN TKVMNMEESN NGSLSAEFKH LTLREQRCGN
 430        440        450        460        470        480
GGRANCDASL IVTEELHLIT FETEVYHQGL KIDLETHSLP VVVISNICQM PNAWASILWY
 490        500        510        520        530        540
NMLTNNPKNV NFFTKPPIGT WDQVAEVLSW QFSSTTKRGL SIEQLTTLAE KLLGPGVNYS
 550        560        570        580        590        600
GCQITWAKFC KENMAGKGFS FWVWLDNIID LVKKYILALW NEGYIMGFIS KERERAILST
 610        620        630        640        650        660
KPPGTFLLRF SESSKEGGVT FTWVEKDISG KTQIQSVEPY TKQQLNNMSF AEIIMGYKIM
 670        680        690        700        710        720
DATNILVSPL VYLYPDIPKE EAFGKYCRPE SQEHPEADPG SAAPYLKTKF ICVTPTTCSN
 730        740        750        760        770
TIDLPMSPRT LDSLMQFGNN GEGAEPSAGG QFESLTFDME LTSECATSPM
```

FIG. 8

```
             10         20         30         40         50         60
     MEGAGGANDK KKISSERRKE KSRDAARSRR SKESEVFYEL AHQLPLPHNV SSHLDKASVM
             70         80         90        100        110        120
     RLTISYLRVR KLLDAGDLDI EDDMKAQMNC FYLKALDGFV MVLTDDGDMI YISDNVNKYM
            130        140        150        160        170        180
     GLTQFELTGH SVFDFTHPCD HEEMREMLTH RNGLVKKGKE QNTQRSFFLR MKCTLTSRGR
            190        200        210        220        230        240
     TMNIKSATWK VLHCTGHIHV YDTNSNQPQC GYKKPPMTCL VLICEPIPHP SNIEIPLDSK
            250        260        270        280        290        300
     TFLSRHSLDM KFSYCDERIT ELMGYEPEEL LGRSIYEYYH ALDSDHLTKT HHDMFTKGQV
            310        320        330        340        350        360
     TTGQYRMLAK RGGYVWVETQ ATVIYNTKNS QPQCTVCVNY VVSGIIQHDL IFSLQQTECV
            370        380        390        400        410        420
     LKPVESSDMK MTQLFTKVES EDTSSLFDKL APAAGDTIIS LDFGSNDTET
            430        440        450        460        470        480
     DDQLEEVPL  YNDVMLPSPN EKLQNINLAM SPLPTAETPK PLRSSADPAL NQEVALKLEP
            490        500        510        520        530        540
     NPESLELSFT MPQIQDQTPS PSDGSTRQSS PEPNSPSEYC FYVDSDMVNE FKLELVEKLF
            550        560        570        580        590        600
     AEDTEAKNPF STQDTDLDLE MLAPYIPMDD DFQLRSFDQL SPLESSSASP ESASPQSTVT
            610        620        630        640        650        660
     VFQQTQIQEP TANATTTTAT TDELKTVTKD RMEDIKILIA SPSPTHIHKE TTSATSSPYR
            670        680        690        700        710        720
     DTQSRTASPN RAGKGVIEQT EKSHPRSPNV LSVALSQRTT VPEEEINPKI LALQNAQRKR
            730        740        750        760        770        780
     KMEHDGSLFQ AVGIGTLLQQ PDDHAATTSL SWKRVKGCKS SEQNGMEQKT IILIPSDLAC
            790        800        810        820
     RLLGQSMDES GLPQLTSYDC EVNAPIQGSR NLLQGEELLR ALDQVN
```

FIG. 9

```
        10              20              30              40              50              60
MQRLVAWDPA      CLPLPPPPPA      FKSMEVANFY      YEADCLAAAY      GGKAAPAAPP      AARPGPRPPA
        70              80              90             100             110             120
GELGSIGDHE      RAIDFSPYLE      PLGAPQAPAP      ATATDTFEAA      PPAPAPAPAS      SGQHHDFLSD
       130             140             150             160             170             180
LFSDDYGGKN      CKKPAEYGYV      SLGRLGAAKG      ALHPGCFAPL      HPPPPPPPPP      AELKAEPGFE
       190             200             210             220             230             240
PADCKRKEEA      GAPGGGAGMA      AGFPYALRAY      LGYQAVPSGS      SGSLSTSSSS      SPPGTPSPAD
       250             260             270             280             290             300
AKAPPTACYA      GAAPAPSQVK      SKAKKTVDKH      SDEYKIRRER      NNIAVRKSRD      KAKMRNLETQ
       310             320             330             340
HKVLELTAEN      ERLQKKVEQL      SRELSTLRNL      FKQLPEPLLA      SSGHC
```

FIG. 10

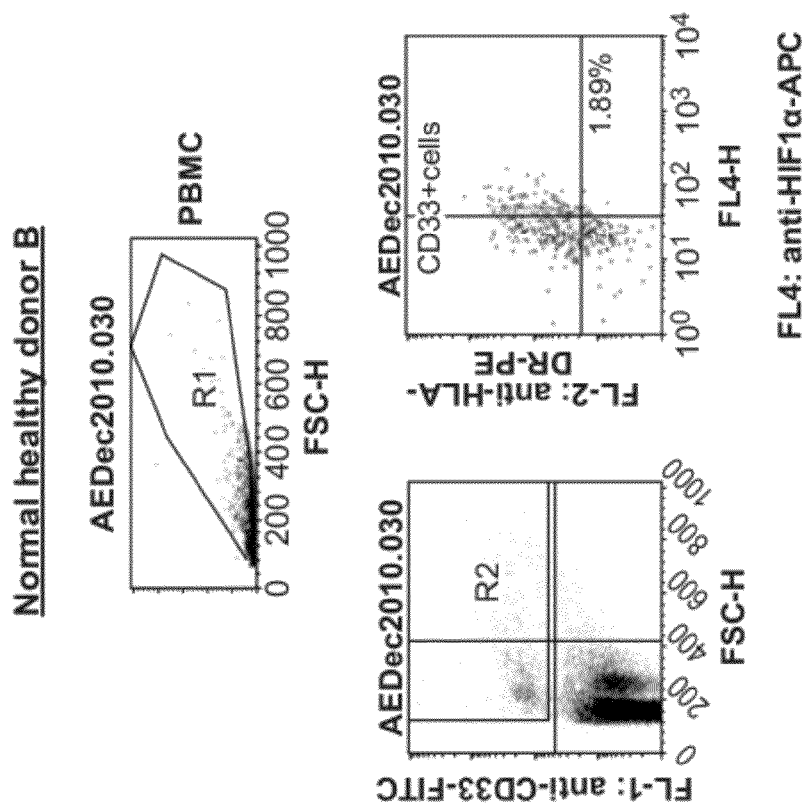
FIG. 11B (Cont. 1)

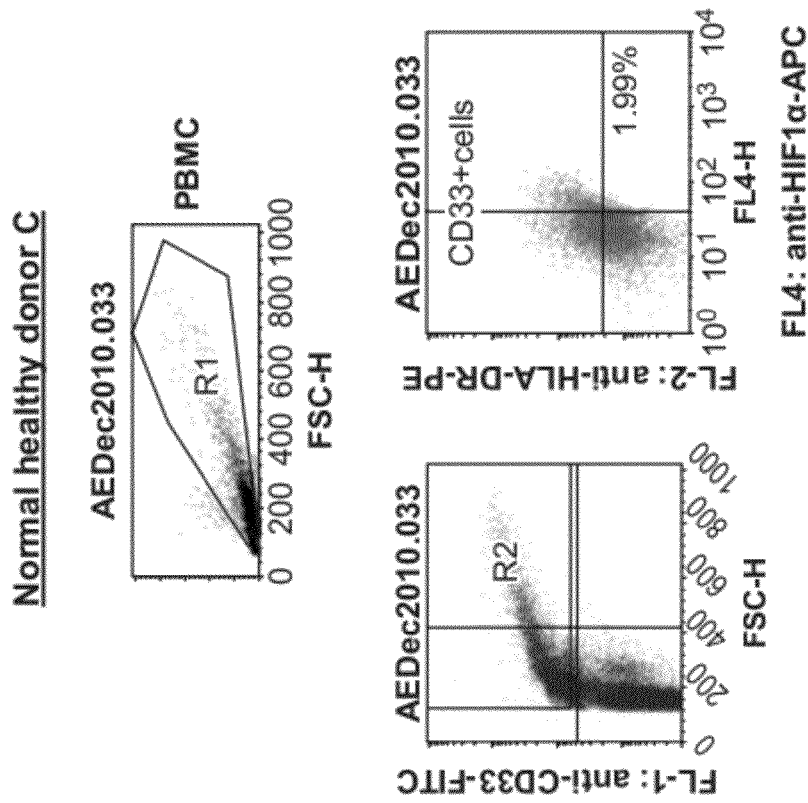
FIG. 11B (Cont. 2)

US 8,883,497 B2

SEQUENCE LISTING

<160> NUMBER OF SEQ ID NOS: 3

<210> SEQ ID NO 1
<211> LENGTH: 770
<212> TYPE: PRT
<213> ORGANISM: Homo sapiens

<400> SEQUENCE: 1

```
Met Ala Gln Trp Asn Gln Leu Gln Gln Leu Asp Thr Arg Tyr Leu Glu
1               5                   10                  15

Gln Leu His Gln Leu Tyr Ser Asp Ser Phe Pro Met Glu Leu Arg Gln
            20                  25                  30

Phe Leu Ala Pro Trp Ile Glu Ser Gln Asp Trp Ala Tyr Ala Ala Ser
        35                  40                  45

Lys Glu Ser His Ala Thr Leu Val Phe His Asn Leu Leu Gly Glu Ile
    50                  55                  60

Asp Gln Gln Tyr Ser Arg Phe Leu Gln Glu Ser Asn Val Leu Tyr Gln
65                  70                  75                  80

His Asn Leu Arg Arg Ile Lys Gln Phe Leu Gln Ser Arg Tyr Leu Glu
                85                  90                  95

Lys Pro Met Glu Ile Ala Arg Ile Val Ala Arg Cys Leu Trp Glu Glu
            100                 105                 110

Ser Arg Leu Leu Gln Thr Ala Ala Thr Ala Ala Gln Gln Gly Gly Gln
        115                 120                 125

Ala Asn His Pro Thr Ala Ala Val Val Thr Glu Lys Gln Gln Met Leu
    130                 135                 140

Glu Gln His Leu Gln Asp Val Arg Lys Arg Val Gln Asp Leu Glu Gln
145                 150                 155                 160

Lys Met Lys Val Val Glu Asn Leu Gln Asp Asp Phe Asp Phe Asn Tyr
                165                 170                 175

Lys Thr Leu Lys Ser Gln Gly Asp Met Gln Asp Leu Asn Gly Asn Asn
            180                 185                 190

Gln Ser Val Thr Arg Gln Lys Met Gln Gln Leu Glu Gln Met Leu Thr
```

```
                195                 200                 205
Ala Leu Asp Gln Met Arg Arg Ser Ile Val Ser Glu Leu Ala Gly Leu
210                 215                 220

Leu Ser Ala Met Glu Tyr Val Gln Lys Thr Leu Thr Asp Glu Glu Leu
225                 230                 235                 240

Ala Asp Trp Lys Arg Gln Gln Ile Ala Cys Ile Gly Gly Pro Pro
                245                 250                 255

Asn Ile Cys Leu Asp Arg Leu Glu Asn Trp Ile Thr Ser Leu Ala Glu
                260                 265                 270

Ser Gln Leu Gln Thr Arg Gln Gln Ile Lys Lys Leu Glu Glu Leu Gln
                275                 280                 285

Gln Lys Val Ser Tyr Lys Gly Asp Pro Ile Val Gln His Arg Pro Met
290                 295                 300

Leu Glu Glu Arg Ile Val Glu Leu Phe Arg Asn Leu Met Lys Ser Ala
305                 310                 315                 320

Phe Val Val Glu Arg Gln Pro Cys Met Pro Met His Pro Asp Arg Pro
                325                 330                 335

Leu Val Ile Lys Thr Gly Val Gln Phe Thr Thr Lys Val Arg Leu Leu
                340                 345                 350

Val Lys Phe Pro Glu Leu Asn Tyr Gln Leu Lys Ile Lys Val Cys Ile
                355                 360                 365

Asp Lys Asp Ser Gly Asp Val Ala Ala Leu Arg Gly Ser Arg Lys Phe
370                 375                 380

Asn Ile Leu Gly Thr Asn Thr Lys Val Met Asn Met Glu Glu Ser Asn
385                 390                 395                 400

Asn Gly Ser Leu Ser Ala Glu Phe Lys His Leu Thr Leu Arg Glu Gln
                405                 410                 415

Arg Cys Gly Asn Gly Gly Arg Ala Asn Cys Asp Ala Ser Leu Ile Val
                420                 425                 430

Thr Glu Glu Leu His Leu Ile Thr Phe Glu Thr Glu Val Tyr His Gln
                435                 440                 445

Gly Leu Lys Ile Asp Leu Glu Thr His Ser Leu Pro Val Val Val Ile
450                 455                 460

Ser Asn Ile Cys Gln Met Pro Asn Ala Trp Ala Ser Ile Leu Trp Tyr
465                 470                 475                 480

Asn Met Leu Thr Asn Asn Pro Lys Asn Val Asn Phe Phe Thr Lys Pro
                485                 490                 495

Pro Ile Gly Thr Trp Asp Gln Val Ala Glu Val Leu Ser Trp Gln Phe
                500                 505                 510

Ser Ser Thr Thr Lys Arg Gly Leu Ser Ile Glu Gln Leu Thr Thr Leu
                515                 520                 525

Ala Glu Lys Leu Leu Gly Pro Gly Val Asn Tyr Ser Gly Cys Gln Ile
530                 535                 540

Thr Trp Ala Lys Phe Cys Lys Glu Asn Met Ala Gly Lys Gly Phe Ser
545                 550                 555                 560

Phe Trp Val Trp Leu Asp Asn Ile Ile Asp Leu Val Lys Lys Tyr Ile
                565                 570                 575

Leu Ala Leu Trp Asn Glu Gly Tyr Ile Met Gly Phe Ile Ser Lys Glu
                580                 585                 590

Arg Glu Arg Ala Ile Leu Ser Thr Lys Pro Pro Gly Thr Phe Leu Leu
                595                 600                 605

Arg Phe Ser Glu Ser Ser Lys Glu Gly Gly Val Thr Phe Thr Trp Val
                610                 615                 620
```

-continued

```
Glu Lys Asp Ile Ser Gly Lys Thr Gln Ile Gln Ser Val Glu Pro Tyr
625                 630                 635                 640

Thr Lys Gln Gln Leu Asn Asn Met Ser Phe Ala Glu Ile Ile Met Gly
            645                 650                 655

Tyr Lys Ile Met Asp Ala Thr Asn Ile Leu Val Ser Pro Leu Val Tyr
        660                 665                 670

Leu Tyr Pro Asp Ile Pro Lys Glu Glu Ala Phe Gly Lys Tyr Cys Arg
    675                 680                 685

Pro Glu Ser Gln Glu His Pro Glu Ala Asp Pro Gly Ser Ala Ala Pro
690                 695                 700

Tyr Leu Lys Thr Lys Phe Ile Cys Val Thr Pro Thr Thr Cys Ser Asn
705                 710                 715                 720

Thr Ile Asp Leu Pro Met Ser Pro Arg Thr Leu Asp Ser Leu Met Gln
            725                 730                 735

Phe Gly Asn Asn Gly Glu Gly Ala Glu Pro Ser Ala Gly Gly Gln Phe
        740                 745                 750

Glu Ser Leu Thr Phe Asp Met Glu Leu Thr Ser Glu Cys Ala Thr Ser
    755                 760                 765

Pro Met
    770

<210> SEQ ID NO 2
<211> LENGTH: 826
<212> TYPE: PRT
<213> ORGANISM: Homo sapiens

<400> SEQUENCE: 2

Met Glu Gly Ala Gly Gly Ala Asn Asp Lys Lys Lys Ile Ser Ser Glu
1               5                   10                  15

Arg Arg Lys Glu Lys Ser Arg Asp Ala Ala Arg Ser Arg Arg Ser Lys
            20                  25                  30

Glu Ser Glu Val Phe Tyr Glu Leu Ala His Gln Leu Pro Leu Pro His
        35                  40                  45

Asn Val Ser Ser His Leu Asp Lys Ala Ser Val Met Arg Leu Thr Ile
    50                  55                  60

Ser Tyr Leu Arg Val Arg Lys Leu Leu Asp Ala Gly Asp Leu Asp Ile
65                  70                  75                  80

Glu Asp Asp Met Lys Ala Gln Met Asn Cys Phe Tyr Leu Lys Ala Leu
                85                  90                  95

Asp Gly Phe Val Met Val Leu Thr Asp Asp Gly Asp Met Ile Tyr Ile
            100                 105                 110

Ser Asp Asn Val Asn Lys Tyr Met Gly Leu Thr Gln Phe Glu Leu Thr
        115                 120                 125

Gly His Ser Val Phe Asp Phe Thr His Pro Cys Asp His Glu Glu Met
    130                 135                 140

Arg Glu Met Leu Thr His Arg Asn Gly Leu Val Lys Lys Gly Lys Glu
145                 150                 155                 160

Gln Asn Thr Gln Arg Ser Phe Phe Leu Arg Met Lys Cys Thr Leu Thr
                165                 170                 175

Ser Arg Gly Arg Thr Met Asn Ile Lys Ser Ala Thr Trp Lys Val Leu
            180                 185                 190

His Cys Thr Gly His Ile His Val Tyr Asp Thr Asn Ser Asn Gln Pro
        195                 200                 205

Gln Cys Gly Tyr Lys Lys Pro Pro Met Thr Cys Leu Val Leu Ile Cys
```

```
              210                 215                 220
Glu Pro Ile Pro His Pro Ser Asn Ile Glu Ile Pro Leu Asp Ser Lys
225                 230                 235                 240

Thr Phe Leu Ser Arg His Ser Leu Asp Met Lys Phe Ser Tyr Cys Asp
                    245                 250                 255

Glu Arg Ile Thr Glu Leu Met Gly Tyr Glu Pro Glu Glu Leu Leu Gly
                260                 265                 270

Arg Ser Ile Tyr Glu Tyr Tyr His Ala Leu Asp Ser Asp His Leu Thr
            275                 280                 285

Lys Thr His His Asp Met Phe Thr Lys Gly Gln Val Thr Thr Gly Gln
        290                 295                 300

Tyr Arg Met Leu Ala Lys Arg Gly Gly Tyr Val Trp Val Glu Thr Gln
305                 310                 315                 320

Ala Thr Val Ile Tyr Asn Thr Lys Asn Ser Gln Pro Gln Cys Ile Val
                    325                 330                 335

Cys Val Asn Tyr Val Val Ser Gly Ile Ile Gln His Asp Leu Ile Phe
                340                 345                 350

Ser Leu Gln Gln Thr Glu Cys Val Leu Lys Pro Val Glu Ser Ser Asp
            355                 360                 365

Met Lys Met Thr Gln Leu Phe Thr Lys Val Glu Ser Glu Asp Thr Ser
        370                 375                 380

Ser Leu Phe Asp Lys Leu Lys Lys Glu Pro Asp Ala Leu Thr Leu Leu
385                 390                 395                 400

Ala Pro Ala Ala Gly Asp Thr Ile Ile Ser Leu Asp Phe Gly Ser Asn
                    405                 410                 415

Asp Thr Glu Thr Asp Asp Gln Gln Leu Glu Glu Val Pro Leu Tyr Asn
                420                 425                 430

Asp Val Met Leu Pro Ser Pro Asn Glu Lys Leu Gln Asn Ile Asn Leu
            435                 440                 445

Ala Met Ser Pro Leu Pro Thr Ala Glu Thr Pro Lys Pro Leu Arg Ser
        450                 455                 460

Ser Ala Asp Pro Ala Leu Asn Gln Glu Val Ala Leu Lys Leu Glu Pro
465                 470                 475                 480

Asn Pro Glu Ser Leu Glu Leu Ser Phe Thr Met Pro Gln Ile Gln Asp
                    485                 490                 495

Gln Thr Pro Ser Pro Ser Asp Gly Ser Thr Arg Gln Ser Ser Pro Glu
                500                 505                 510

Pro Asn Ser Pro Ser Glu Tyr Cys Phe Tyr Val Asp Ser Asp Met Val
            515                 520                 525

Asn Glu Phe Lys Leu Glu Leu Val Glu Lys Leu Phe Ala Glu Asp Thr
        530                 535                 540

Glu Ala Lys Asn Pro Phe Ser Thr Gln Asp Thr Asp Leu Asp Leu Glu
545                 550                 555                 560

Met Leu Ala Pro Tyr Ile Pro Met Asp Asp Asp Phe Gln Leu Arg Ser
                    565                 570                 575

Phe Asp Gln Leu Ser Pro Leu Glu Ser Ser Ser Ala Ser Pro Glu Ser
                580                 585                 590

Ala Ser Pro Gln Ser Thr Val Thr Val Phe Gln Gln Thr Gln Ile Gln
            595                 600                 605

Glu Pro Thr Ala Asn Ala Thr Thr Thr Thr Ala Thr Thr Asp Glu Leu
        610                 615                 620

Lys Thr Val Thr Lys Asp Arg Met Glu Asp Ile Lys Ile Leu Ile Ala
625                 630                 635                 640
```

```
Ser Pro Ser Pro Thr His Ile His Lys Glu Thr Thr Ser Ala Thr Ser
            645                 650                 655

Ser Pro Tyr Arg Asp Thr Gln Ser Arg Thr Ala Ser Pro Asn Arg Ala
            660                 665                 670

Gly Lys Gly Val Ile Glu Gln Thr Glu Lys Ser His Pro Arg Ser Pro
            675                 680                 685

Asn Val Leu Ser Val Ala Leu Ser Gln Arg Thr Thr Val Pro Glu Glu
            690                 695                 700

Glu Leu Asn Pro Lys Ile Leu Ala Leu Gln Asn Ala Gln Arg Lys Arg
705                 710                 715                 720

Lys Met Glu His Asp Gly Ser Leu Phe Gln Ala Val Gly Ile Gly Thr
            725                 730                 735

Leu Leu Gln Gln Pro Asp Asp His Ala Ala Thr Thr Ser Leu Ser Trp
            740                 745                 750

Lys Arg Val Lys Gly Cys Lys Ser Ser Glu Gln Asn Gly Met Glu Gln
            755                 760                 765

Lys Thr Ile Ile Leu Ile Pro Ser Asp Leu Ala Cys Arg Leu Leu Gly
770                 775                 780

Gln Ser Met Asp Glu Ser Gly Leu Pro Gln Leu Thr Ser Tyr Asp Cys
785                 790                 795                 800

Glu Val Asn Ala Pro Ile Gln Gly Ser Arg Asn Leu Leu Gln Gly Glu
            805                 810                 815

Glu Leu Leu Arg Ala Leu Asp Gln Val Asn
            820                 825

<210> SEQ ID NO 3
<211> LENGTH: 345
<212> TYPE: PRT
<213> ORGANISM: Homo sapiens

<400> SEQUENCE: 3

Met Gln Arg Leu Val Ala Trp Asp Pro Ala Cys Leu Pro Leu Pro Pro
1               5                   10                  15

Pro Pro Pro Ala Phe Lys Ser Met Glu Val Ala Asn Phe Tyr Tyr Glu
            20                  25                  30

Ala Asp Cys Leu Ala Ala Ala Tyr Gly Gly Lys Ala Ala Pro Ala Ala
            35                  40                  45

Pro Pro Ala Ala Arg Pro Gly Pro Arg Pro Pro Ala Gly Glu Leu Gly
        50                  55                  60

Ser Ile Gly Asp His Glu Arg Ala Ile Asp Phe Ser Pro Tyr Leu Glu
65                  70                  75                  80

Pro Leu Gly Ala Pro Gln Ala Pro Ala Pro Ala Thr Ala Thr Asp Thr
            85                  90                  95

Phe Glu Ala Ala Pro Pro Ala Pro Ala Pro Ala Pro Ala Ser Ser Gly
            100                 105                 110

Gln His His Asp Phe Leu Ser Asp Leu Phe Ser Asp Asp Tyr Gly Gly
            115                 120                 125

Lys Asn Cys Lys Lys Pro Ala Glu Tyr Gly Tyr Val Ser Leu Gly Arg
        130                 135                 140

Leu Gly Ala Ala Lys Gly Ala Leu His Pro Gly Cys Phe Ala Pro Leu
145                 150                 155                 160

His Pro Pro Pro Pro Pro Pro Pro Ala Glu Leu Lys Ala Glu
            165                 170                 175

Pro Gly Phe Glu Pro Ala Asp Cys Lys Arg Lys Glu Glu Ala Gly Ala
```

-continued

```
                180                 185                 190
Pro Gly Gly Gly Ala Gly Met Ala Ala Gly Phe Pro Tyr Ala Leu Arg
        195                 200                 205

Ala Tyr Leu Gly Tyr Gln Ala Val Pro Ser Gly Ser Ser Gly Ser Leu
        210                 215                 220

Ser Thr Ser Ser Ser Ser Ser Pro Pro Gly Thr Pro Ser Pro Ala Asp
225                 230                 235                 240

Ala Lys Ala Pro Pro Thr Ala Cys Tyr Ala Gly Ala Ala Pro Ala Pro
                245                 250                 255

Ser Gln Val Lys Ser Lys Ala Lys Lys Thr Val Asp Lys His Ser Asp
                260                 265                 270

Glu Tyr Lys Ile Arg Arg Glu Arg Asn Asn Ile Ala Val Arg Lys Ser
            275                 280                 285

Arg Asp Lys Ala Lys Met Arg Asn Leu Glu Thr Gln His Lys Val Leu
        290                 295                 300

Glu Leu Thr Ala Glu Asn Glu Arg Leu Gln Lys Lys Val Glu Gln Leu
305                 310                 315                 320

Ser Arg Glu Leu Ser Thr Leu Arg Asn Leu Phe Lys Gln Leu Pro Glu
                325                 330                 335

Pro Leu Leu Ala Ser Ser Gly His Cys
                340                 345
```

HUMAN MYELOID DERIVED SUPPRESSOR CELL CANCER MARKERS

CROSS-REFERENCE TO RELATED APPLICATIONS

This application claims priority under 35 U.S.C. §119(e) to U.S. Provisional Application Ser. No. 61/480,311 filed Apr. 28, 2011 and U.S. Provisional Application Ser. No. 61/567,042 filed Dec. 5, 2011, the contents of which are each incorporated by reference into the present disclosure.

SEQUENCE LISTING

The instant application contains a Sequence Listing which has been submitted in ASCII format via EFS-Web and is hereby incorporated by reference in its entirety. Said ASCII copy, created on Jun. 6, 2012, is named 75405170.txt and is 17,046 bytes in size.

BACKGROUND

Early detection of cancer or its recurrence is tantamount to a good health outcome. Identifying markers that surface at an early stage allow the oncologist to more successfully treat the cancer patient.

Immune suppressor cells, such as myeloid-derived suppressor cells (MDSC), contribute to tumor immune tolerance and the failure of immunotherapy regimens in cancer patients and experimental tumor models (1). MDSC reportedly inhibit T cell effector functions through a range of mechanisms, including: arginase 1 (ARG-1)-mediated depletion of L-arginine (2); inducible nitric oxide synthase (iNOS) and NADPH oxidase (NOX2) production of reactive nitrogen and oxygen species (3, 4); vascular endothelial growth factor over-expression (5); cysteine depletion (6); and the expansion of T-regulatory (Treg) cell populations (7, 8). While rare or absent in healthy subjects, MDSC accumulate in the settings of trauma, severe infection or sepsis, and cancer (9), possibly as a result of the hypoxic environment and hypoxia-inducible factor (HIF)-1α expression (10). MDSC have been described in patients with colon carcinoma (11), melanoma (11), hepatocellular carcinoma (12), head and neck squamous cell carcinoma (4), non-small cell lung carcinoma (13), renal cell carcinoma (14), pancreatic adenocarcinoma (15) and breast carcinoma (16). In cancer patients, Diaz, et al. (16) propose that accumulation of MDSC correlates with more advanced disease and poor prognosis. The ability to detect characteristic MDSC in cancer patients would allow the oncologist to determine the effectiveness of therapy and if tumor recurrence has occurred after treatment. Furthermore, MDSC characterization in peripheral blood could be used to differentiate between benign and malignant lesions and masses which can be difficult to discern by routine imaging, fine needle aspiration biopsies, or existing serum assays. Thus, there is a need in the art for methods of identifying MDSC populations so that the appropriate treatment regimine can be prescribed. This invention satisfies this need and provides related advantages as well.

SUMMARY

Provided herein are methods for identifying MDSC populations from subject samples and treating a subject with cancer comprising, or alternatively consisting essentially of or yet further consisting of: a) detecting, in a cell-containing sample from said subject, myeloid-derived suppressor cells (MDSC), wherein said MDSC have a phenotype of the group $CD33^+HLA\text{-}DR^{low}HIF1\alpha^+/STAT3^+$, $CD14^+HLA\text{-}DR^{low}HIF1\alpha^+/STAT3^+/pSTAT3^+/C/EBPb^+$, $CD66b^+HLA\text{-}DR^{low}HIF1\alpha^+/STAT3^+/pSTAT3^+/C/EBPb^+$, $CD33^+HLA\text{-}DR^{low}HIF1\alpha^+/STAT3^+/pSTAT3^+/C/EBPb^+$, $CD11b^+HLA\text{-}DR^{low}HIF1\alpha^+/STAT3^+/pSTAT3^+/C/EBPb^+$, or $CD11b^+HLA\text{-}DR^{low}C/EBP\beta^+$; and, b) if said MDSC are detected, administering a cancer therapeutic and not treating the patient if such a phenotype is not detected. In another aspect, a method for treating a cancer patient determined to be likely responsive to the method is provided, the method comprising, or alternatively consisting essentially of, or yet further consisting of, administering to the patient an effective amount of a cancer therapy, wherein the patient was determined to be likely responsive by screening a cell or tissue isolated from the patient for a myeloid-derived suppressor cells (MDSC), wherein said MDSC have a phenotype of the group $CD33^+HLA\text{-}DR^{low}HIF1\alpha^+/STAT3^+$, $CD14^+HLA\text{-}DR^{low}HIF1\alpha^+/STAT3^+/pSTAT3^+/C/EBPb^+$, $CD66b^+HLA\text{-}DR^{low}HIF1\alpha^+/STAT3^+/pSTAT3^+/C/EBPb^+$, $CD33^+HLA\text{-}DR^{low}HIF1\alpha^+/STAT3^+/pSTAT3^+/C/EBPb^+$, $CD11b^+HLA\text{-}DR^{low}HIF1\alpha^+/STAT3^+/pSTAT3^+/C/EBPb^+$, or $CD11b^+HLA\text{-}DR^{low}C/EBP\beta^+$.

A further aspect relates to a method of treating a cancer subject determined to be responsive to the treatment, comprising administering to the subject an effective amount of a cancer therapeutic, wherein the cancer subject is determined to be responsive to the therapy by a method comprising detecting, in a cell-containing sample from said subject, myeloid-derived suppressor cells (MDSC) having a phenotype of the group $CD33^+HLA\text{-}DR^{low}HIF1\alpha^+/STAT3^+$, $CD14^+HLA\text{-}DR^{low}HIF1\alpha^+/STAT3^+/pSTAT3^+/C/EBPb^+$, $CD66b^+HLA\text{-}DR^{low}HIF1\alpha^+/STAT3^+/pSTAT3^+/C/EBPb^+$, $CD33^+HLA\text{-}DR^{low}HIF1\alpha^+/STAT3^+/pSTAT3^+/C/EBPb^+$, $CD11b^+HLA\text{-}DR^{low}HIF1\alpha^+/STAT3^+/pSTAT3^+/C/EBPb^+$, and $CD11b^+HLA\text{-}DR^{low}C/EBP\beta^+$.

Another aspect relates to a method for detecting the presence of cancer or aiding in the detecting of cancer in a subject comprising, or alternatively consisting essentially of, or yet further consisting of detecting, in a cell-containing sample from the subject, myeloid-derived suppressor cells (MDSC), wherein the MDSC have a phenotype of the group $CD33^+HLA\text{-}DR^{low}HIF1\alpha^+/STAT3^+$, $CD14^+HLA\text{-}DR^{low}HIF1\alpha^+/STAT3^+/pSTAT3^+/C/EBPb^+$, $CD66b^+HLA\text{-}DR^{low}HIF1\alpha^+/STAT3^+/pSTAT3^+/C/EBPb^+$, $CD33^+HLA\text{-}DR^{low}HIF1\alpha^+/STAT3^+/pSTAT3^+/C/EBPb^+$, $CD11b^+HLA\text{-}DR^{low}HIF1\alpha^+/STAT3^+/pSTAT3^+/C/EBPb^+$, and $CD11b^+HLA\text{-}DR^{low}C/EBP\beta^+$; and wherein the presence of the MDSC indicates the likely presence of cancer and the absent of MDSC indicates that the presence of the cancer is not likely.

A further aspect relates to a method for determining the efficacy of a cancer treatment in a subject having cancer, said method comprising, or alternatively consisting essentially of, or yet further consisting of, detecting, in a cell-containing sample from the subject, myeloid-derived suppressor cells (MDSC), wherein said MDSC have a phenotype of the group $CD33^+HLA\text{-}DR^{low}HIF1\alpha^+/STAT3^+$, $CD14^+HLA\text{-}DR^{low}HIF1\alpha^+/STAT3^+/pSTAT3^+/C/EBPb^+$, $CD66b^+HLA\text{-}DR^{low}HIF1\alpha^+/STAT3^+/pSTAT3^+/C/EBPb^+$, $CD33^+HLA\text{-}DR^{low}HIF1\alpha^+/STAT3^+/pSTAT3^+/C/EBPb^+$, $CD11b^+HLA\text{-}DR^{low}HIF1\alpha^+/STAT3^+/pSTAT3^+/C/EBPb^+$, and $CD11b^+HLA\text{-}DR^{low}C/EBP\beta^+$; and wherein a decrease or absence of said MDSC during cancer therapy indicates an effective therapeutic response and an increase or presence of the MDSC during cancer therapy indicates an ineffective therapeutic response.

A further aspect relates to a method for generating human MDSC from a source of myeloid lineage cells comprising, or alternatively consisting essentially of, or yet further consisting of: (a) contacting the source of myeloid lineage cells with a tumor sample under conditions sufficient to induce MDSC; and, (b) isolating the MDSC. The isolated MDSC and compositions containing the cells are further provided herein.

BRIEF DESCRIPTION OF THE DRAWINGS

FIG. 8. Amino acid sequence of STAT3 (SEQ. ID. NO. 1).
FIG. 9. Amino acid sequence of HIF1α (SEQ. ID. NO. 2).
FIG. 10. Amino acid sequence of C/EBPβ (SEQ. ID. NO. 3).

Figure 1:
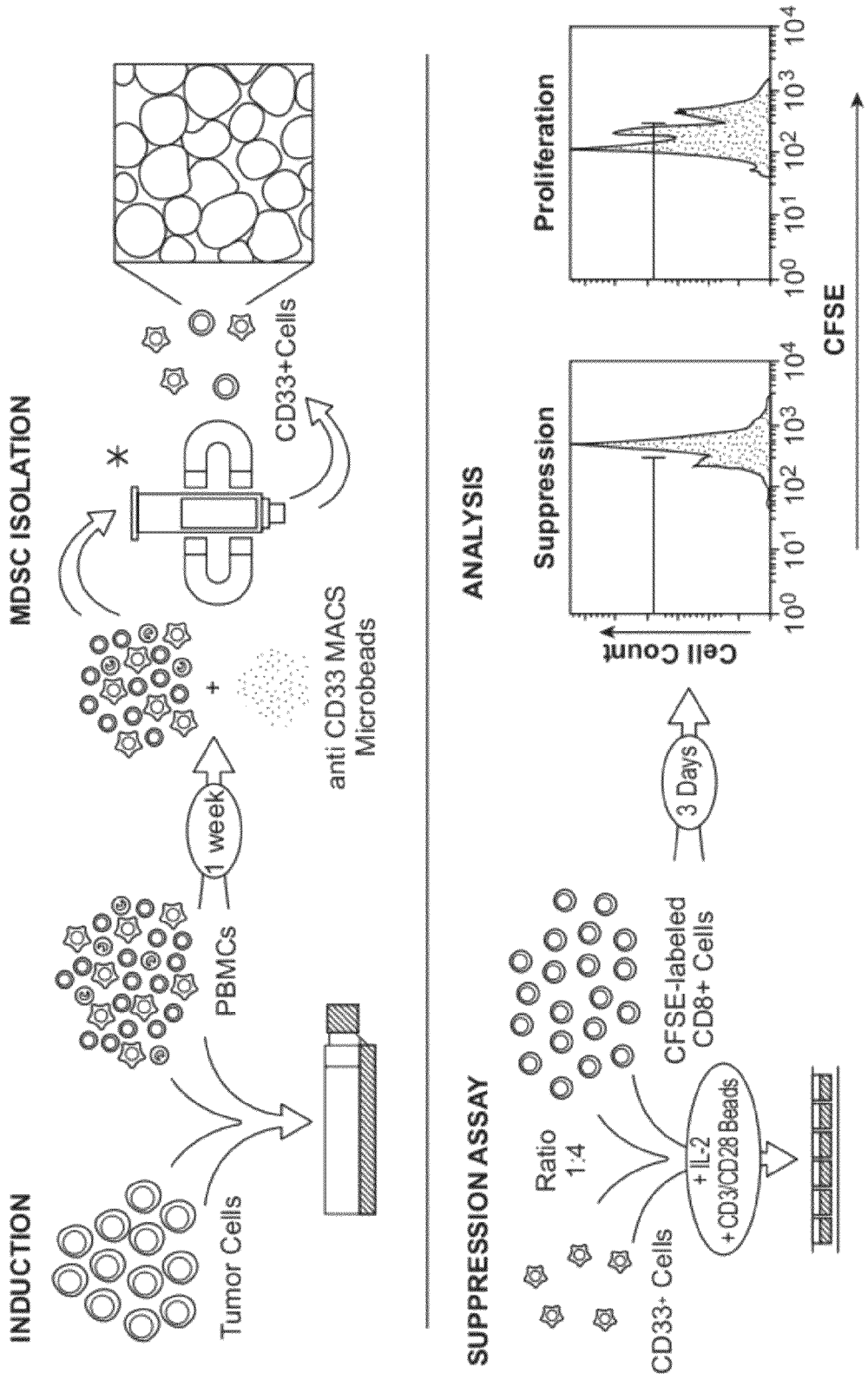
FIG. 1. Schematic of Co-culture and MDSC Suppression Assays for the in vitro generation of tumor-associated myeloid suppressor cells. Induction: Normal donor peripheral blood mononuclear cell (PBMC) are co-cultured with human solid tumor cell lines for one week. MDSC Isolation: CD33+ cells are isolated from PBMC-tumor co-cultures by anti-CD33 microbead labeling and magnetic column separation. Suppression Assay: Tumor-educated CD33$^+$ cells are subsequently co-cultured with fresh, autologous CFSE-labeled CD8$^+$ T cells at a 1:4 ratio in the presence of T cell stimuli. After 3 days, T cell proliferation is measured as carboxyfluorescein succinimidyl ester (CFSE)-dilution using flow cytometry. Suppressive function is evaluated as the ability of CD33$^+$ cells to inhibit autologous CD8$^+$ T cell proliferation.
Figure 2:
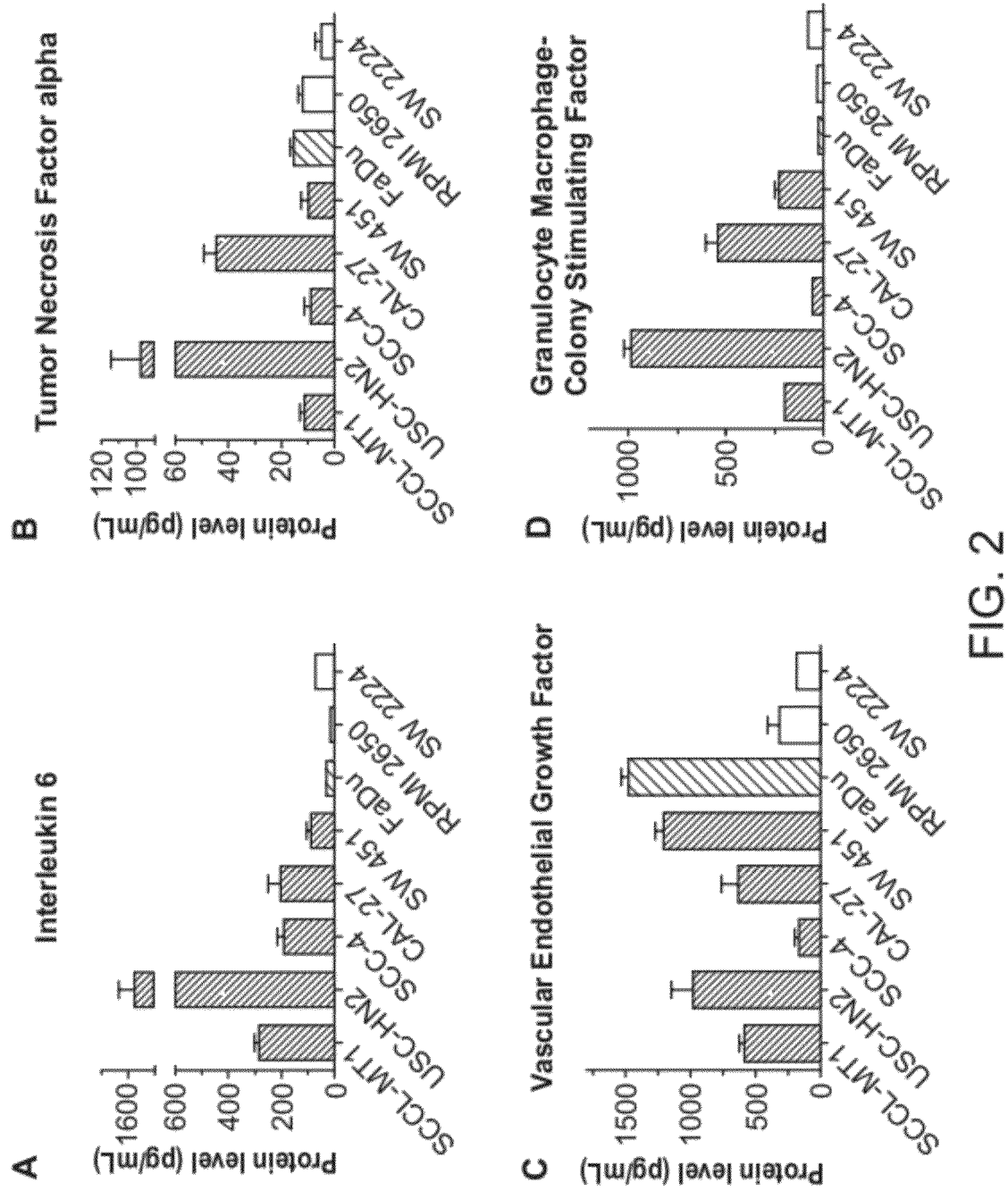
FIG. 2. CD33$^+$ MDSC induced by subset MDSC-inducing cell lines produce increased IL-1β, IL-6 (A), TNFα (B), VEGF (C) and GM-CSF (D). Protein secretion of these cytokines by head and neck squamous cell carcinoma (HNSCC) cell lines was measured in supernatants using ELISA techniques to confirm gene expression findings. Mean protein levels shown (n=2, run in triplicate), ±SEM. * indicates statistical significance, $p<0.05$.

| Quad | Events | % Gated | % Total | X Mean | X Geo Mean | Y Mean | Y Geo Mean |
|---|---|---|---|---|---|---|---|
| Normal healthy donor A | | | | | | | |
| UL | 1307 | 38.27 | 2.50 | 20.40 | 18.12 | 81.78 | 60.37 |
| UR | 197 | 5.77 | 0.38 | 51.69 | 50.51 | 152.62 | 108.42 |
| LL | 1907 | 55.84 | 3.64 | 13.31 | 11.41 | 9.06 | 7.32 |
| LR | 4 | 0.12 | 0.01 | 44.66 | 44.51 | 10.69 | 9.69 |
| Normal healthy donor B | | | | | | | |
| UL | 331 | 44.61 | 0.62 | 23.34 | 21.63 | 175.48 | 70.12 |
| UR | 126 | 16.98 | 0.24 | 64.28 | 60.69 | 180.48 | 104.88 |
| LL | 271 | 36.52 | 0.51 | 20.36 | 18.45 | 11.00 | 9.19 |
| LR | 14 | 1.89 | 0.03 | 53.08 | 51.96 | 14.18 | 12.24 |
| Normal healthy donor C | | | | | | | |
| UL | 3407 | 31.08 | 5.70 | 24.13 | 22.73 | 47.64 | 39.61 |
| UR | 1289 | 13.15 | 2.41 | 58.52 | 56.24 | 67.76 | 55.08 |
| LL | 5272 | 53.78 | 9.86 | 20.33 | 18.78 | 11.17 | 9.62 |
| LR | 195 | 1.99 | 0.36 | 46.39 | 45.89 | 14.73 | 13.91 |
| HNSCC Patient A | | | | | | | |
| UL | 898 | 29.25 | 0.93 | 25.10 | 24.72 | 151.56 | 96.11 |
| UR | 628 | 14.16 | 0.65 | 95.85 | 82.39 | 175.14 | 90.75 |
| LL | 2100 | 41.36 | 2.27 | 13.77 | 17.82 | 4.52 | 3.58 |
| LR | 720 | 15.23 | 0.75 | 64.59 | 61.24 | 8.99 | 7.15 |
| HNSCC Patient B | | | | | | | |
| UL | 620 | 20.05 | 1.24 | 24.63 | 23.50 | 138.60 | 80.95 |
| UR | 378 | 10.28 | 0.64 | 102.56 | 89.11 | 222.24 | 87.96 |
| LL | 1655 | 53.00 | 3.33 | 17.12 | 15.39 | 4.67 | 3.55 |
| LR | 488 | 15.78 | 0.98 | 69.30 | 65.12 | 9.13 | 7.43 |

For each FACS analysis run, at least 50,000 live events were counted per sample on a BD FACS Calibur. Data was analyzed using BD CellQuestPro software.

DETAILED DESCRIPTION

As used in the specification and claims, the singular form "a," "an" and "the" include plural references unless the context clearly dictates otherwise. For example, the term "a cell" includes a plurality of cells, including mixtures thereof.

As used herein, the term "comprising" is intended to mean that the compositions and methods include the recited elements, but not excluding others. "Consisting essentially of" when used to define compositions and methods, shall mean excluding other elements of any essential significance to the combination. Thus, a composition consisting essentially of the elements as defined herein would not exclude trace contaminants from the isolation and purification method and pharmaceutically acceptable carriers, such as phosphate buffered saline, preservatives, and the like. "Consisting of" shall mean excluding more than trace elements of other ingredients. Embodiments defined by each of these transition terms are within the scope of this invention.

All numerical designations, e.g., pH, temperature, time, concentration, and molecular weight, including ranges, are approximations which are varied (+) or (−) by increments of 0.1 or 1.0 as is appropriate. It is to be understood, although not always explicitly stated that all numerical designations are preceded by the term "about" which includes a standard deviation of about 15%, or alternatively about 10% or alternatively about 5%. It also is to be understood, although not always explicitly stated, that the reagents described herein are merely exemplary and that equivalents of such are known in the art.

An "effective amount" is an amount sufficient to effect beneficial or desired results. An effective amount can be administered in one or more administrations, applications or dosages. Such delivery is dependent on a number of variables including the time period for which the individual dosage unit is to be used, the bioavailability of the therapeutic agent, the route of administration, etc. It is understood, however, that specific dose levels of the therapeutic agents of the present invention for any particular subject depends upon a variety of factors including the activity of the specific compound employed, bioavailability of the compound, the route of administration, the age of the animal and its body weight, general health, sex, the diet of the animal, the time of administration, the rate of excretion, the drug combination, and the severity of the particular disorder being treated and form of administration. Treatment dosages generally may be titrated to optimize safety and efficacy. Typically, dosage-effect relationships from in vitro and/or in vivo tests initially can provide useful guidance on the proper doses for patient administration. Studies in animal models generally may be used for guidance regarding effective dosages for treatment of diseases. In general, one will desire to administer an amount of the compound that is effective to achieve a serum level commensurate with the concentrations found to be effective in vitro. Thus, where a compound is found to demonstrate in vitro activity, for example as noted in the Tables discussed below one can extrapolate to an effective dosage for administration in vivo. These considerations, as well as effective formulations and administration procedures are well known in the art and are described in standard textbooks. Consistent with this definition and as used herein, the term "therapeutically effective amount" is an amount sufficient to treat a specified disorder or disease or alternatively to obtain a pharmacological response treating a glioblastoma.

As used herein, "treating" or "treatment" of a disease in a patient refers to (1) preventing the symptoms or disease from occurring in an animal that is predisposed or does not yet display symptoms of the disease; (2) inhibiting the disease or arresting its development; or (3) ameliorating or causing regression of the disease or the symptoms of the disease. As understood in the art, "treatment" is an approach for obtaining beneficial or desired results, including clinical results. For the purposes of this invention, beneficial or desired results can include one or more, but are not limited to, alleviation or amelioration of one or more symptoms, diminishment of extent of a condition (including a disease), stabilized (i.e., not worsening) state of a condition (including disease), delay or slowing of condition (including disease), progression, amelioration or palliation of the condition (including disease), states and remission (whether partial or total), whether detectable or undetectable. Preferred are compounds that are potent and can be administered locally at very low doses, thus minimizing systemic adverse effects.

Provided herein are methods comprising, or alternatively consisting essentially of, or yet further consisting of determining the presence of cancer, monitoring the progression of cancer, aiding in the diagnosis of a cancer, monitoring cancer relapse, monitoring the response to cancer therapy, or cancer staging in a subject, by screening or detecting, in a cell-containing sample from the individual, myeloid-derived suppressor cells (MDSC), said MDSC being identified by their expression of CD33, CD14, CD66b, or CD11b and HLA-DR and wherein said identified MDSC are defined by the phenotype CD33$^+$, CD14$^+$, CD66b$^+$, or CD11b$^+$ and HLA-DR$^{low}$. The presence of MDSC with the identified phenotype indicates the presence of cancer or cancer relapse in said individual. A decrease or absence of MDSC during cancer therapy indicates a successful response to therapy in a subject. An increase in MDSC from a baseline cancer diagnosis indicates an advance in cancer stage in a subject. Surprisingly found herein, the following defined phenotypes of human MDSC: CD33$^+$HLA-DR$^{low}$HIF1α$^+$/STAT3$^+$, CD14$^+$HLA-DR$^{low}$HIF1α$^+$/STAT3$^+$/pSTAT3$^+$/C/EBPb$^+$, CD66b$^+$HLA-DR$^{low}$HIF1α$^+$/STAT3$^+$/pSTAT3$^+$/C/EBPb$^+$, CD33$^+$HLA-DR$^{low}$HIF1α$^+$/STAT3$^+$/pSTAT3$^+$/C/EBPb$^+$, CD11b$^+$HLA-DR$^{low}$HIF1α$^+$/STAT3$^+$/pSTAT3$^+$/C/EBPb$^+$, and CD11b$^+$HLA-DR$^{low}$C/EBPβ$^+$), collectively account for the subsets of human MDSC induced by solid tumors and human malignant lymphomas, thereby providing reliable markers for cancer detection and monitoring.

The indicated protein may be expressed on the surface of the cell or within the cell. Additionally, the expression can include all or a portion of the protein.

CD11b is expressed on the surface of many leukocytes involved in the innate immune system, including monocytes, granulocytes, macrophages, and natural killer cells. The following GenBank DNA accession numbers represent the CD11b protein sequence: NP_001139280.1, NP_000623.2, and P11215.2. The sequences represented by each of these GenBank accession numbers is incorporated by reference for all purposes.

CD33 or Siglec-3 is a transmembrane receptor expressed on cells of myeloid lineage. CD33 is usually considered myeloid-specific, but it can also be found on some lymphoid cells. The following GenBank DNA accession numbers represent the CD33 protein sequence: NP_001763.3, NP_001171079.1, NP_001076087.1, P20138.2, CAD36509.1, AAH28152.1, AAK83654.1, EAW71996.1, EAW71995.1, and EAW71994.1. The sequences represented by each of these GenBank accession numbers in incorporated by reference for all purposes.

CD14 is a marker of monocytes in the body, another myeloid-derived population that circulates in peripheral blood. The following GenBank DNA accession numbers represent the CD14 protein sequence: CAG33297.1, AAA51930.1, P08571.2, NP_001167576.1, NP_001167575.1, NP_001035110.1, NP_000582.1, ADX31876.1, AAC83816.1, EAW62037.1, AAH10507.1, and BAG55282.1. The sequences represented by each of these GenBank accession numbers in incorporated by reference for all purposes.

CD66b is a marker of granulocytes in the body, another myeloid-derived population that circulates in peripheral blood. In cancer these myeloid populations may be induced to become suppressive MDSC. The following GenBank DNA accession numbers represent the CD66b protein sequence: AAH26263.1, P31997.2, NP_001806.2, AAC13659.1, and CAB08298.1. The sequences represented by each of these GenBank accession numbers in incorporated by reference for all purposes.

The methods also include determining if a tumor is malignant or benign, aiding in the determination of such diagnosis, cancer prognosis, monitoring the progression of cancer, monitoring cancer relapse, monitoring the response to cancer therapy, or cancer staging in a subject, by evaluating CD33$^+$/HLA-DR$^{low}$, CD14$^+$/HLA-DR$^{low}$, CD66b$^+$/HLA-DR$^{low}$ or, CD11b$^+$/HLA-DR$^{low}$ MDSC for activation of a transcription factor wherein the presence of a MDSC with a cancer-related phenotype of transcription factor activation indicates the presence of cancer or cancer relapse or tumor malignancy in said subject, a decrease or absence of the MDSC during cancer therapy indicates a successful response to therapy in said subject, an increase or persistence in level of said MDSC indicates a reduced survival or early disease recurrence, and an increase in the MDSC indicates an advance in cancer stage in the subject. Transcription factors include, but are not limited to, STAT3, pSTAT3, HIF1α, or C/EBPβ. In an embodiment, the MDSC phenotype is CD33$^+$HLA-DR$^{low}$HIF1α$^+$/STAT3$^+$. In another embodiment, the MDSC phenotype is CD14$^+$HLA-DR$^{low}$HIF1α$^+$/STAT3$^+$/pSTAT3$^+$/C/EBPb$^+$. In another embodiment, the MDSC phenotype is CD66b$^+$HLA-DR$^{low}$HIF1α$^+$/STAT3$^+$/pSTAT3$^+$/C/EBPb$^+$. In another embodiment, the MDSC phenotype is CD33$^+$HLA-DR$^{low}$HIF1α$^+$/STAT3$^+$/pSTAT3$^+$/C/EBPb$^+$. In another embodiment, the MDSC phenotype is CD11b$^+$HLA-DR$^{low}$HIF1α$^+$/STAT3$^+$/pSTAT3$^+$/C/EBPb$^+$. In another embodiment the MDSC phenotype is CD11b$^+$HLA-DR$^{low}$C/EBPβ$^+$. While not wishing to be held by theory, because the induction of MDSC is an early event in tumor growth, the methods can be used to evaluate tumor occurrence, recurrence or regression before detection by standard radiologic imaging methods.

Activation of transcription indicates the presence of cancer. In a subject previously diagnosed with cancer, increased activation indicates further progression of the cancer and advanced stage of cancer. In a subject undergoing cancer therapy, an increased activation indicates a failing therapy. Methods of detecting gene expression are well known in the art.

STAT3: STATs (signal transducers and activators of transcription) are a family of 7 transcription factors that form part of the JAK-STAT signaling cascade. STAT3 is a transcription factor that binds to the interleukin-6 (IL-6)-responsive elements identified in the promoters of various acute-phase protein genes. STAT3 is activated by IL31 through IL31RA. pSTAT3 is the activated and phosphorylated form of STAT3. The STAT3 protein forms a homodimer or a heterodimer with a related family member (at least STAT1). Interacts with IL31RA, NCOA1, PELP1, SIPAR, SOCS7, STATIP1 and TMF1. STAT3 protein interacts with HCV core protein, IL23R in presence of IL23, and, via SH2 domain, with NLK. STAT3 protein interacts with KPNA4 and KPNA5; KPNA4 may be the primary mediator of nuclear import. STAT3 protein interacts with CAV2; the interaction is increased on insulin-induced tyrosine phosphorylation of CAV2 and leads to STAT3 activation. Constitutive nuclear presence of STAT3 is independent of tyrosine phosphorylation. pSTAT3 refers to the phosphorylated form of STAT3. STAT3 is expressed in heart, brain, placenta, lung, liver, skeletal muscle, kidney and pancreas. STAT3 is activated in many cancers and transformed cell lines and is required in cell culture for transformation and blocking of apoptosis. The following GenBank DNA accession numbers represent the STAT3 protein sequence: AAK17196.1, NP_644805.1, NP_003141.2, NP_998827.1, P40763.2, CAA10032.1, AAB84254.1, AAH14482.1, AAH00627.1, AAS66986.1, EAW60826.1, and EAW60824.1. The sequences represented by each of these GenBank accession numbers in incorporated by reference for all purposes.

HIF1α. Hypoxia-inducible factor-1 (HIF1) is a transcription factor found in mammalian cells cultured under reduced oxygen tension that plays an essential role in cellular and systemic homeostatic responses to hypoxia. HIF1 is a heterodimer composed of an alpha subunit and a beta subunit. The beta subunit has been identified as the aryl hydrocarbon receptor nuclear translocator (ARNT). HIF1α encodes the alpha subunit of HIF-1. Overexpression of a natural antisense transcript (aHIF) of this gene has been shown to be associated with nonpapillary renal carcinomas. Two alternative transcripts encoding different isoforms have been identified. HIF1α functions as a master transcriptional regulator of the adaptive response to hypoxia. Under hypoxic conditions HIF1α activates the transcription of over 40 genes, including, erythropoietin, glucose transporters, glycolytic enzymes, vascular endothelial growth factor, and other genes whose protein products increase oxygen delivery or facilitate metabolic adaptation to hypoxia. HIF1α plays an essential role in embryonic vascularization, tumor angiogenesis and pathophysiology of ischemic disease. HIF1α binds to core DNA sequence 5'-[AG]CGTG-3' within the hypoxia response element (HRE) of target gene promoters. Activation of HIF1α requires recruitment of transcriptional coactivators such as CREBPB and EP300. Activity is enhanced by interaction with both, NCOA1 or NCOA2. Interaction with redox regulatory protein APEX seems to activate CTAD and potentiates activation by NCOA1 and CREBBP.

HIF1α is cytoplasmic in normoxia, but accumulates and translocates to the nucleus with HIF1β in response to hypoxia. In addition, under normoxic conditions HIF1α transcription can be up-regulated by inflammatory cytokines and signaling through JAK/STAT or NFκB pathways. HIF1α colocalizes with SUMO1 in the nucleus. HIF1α is expressed in most tissues with highest levels in kidney and heart. HIF1α is overexpressed in the majority of common human cancers and their metastases, due to the presence of intratumoral hypoxia and as a result of mutations in genes encoding oncoproteins and tumor suppressors. The following GenBank DNA accession numbers represent the HIF1α protein sequence: Q16665.1, NP_001230013.1, NP_851397.1, NP_001521.1, and AAH12527.1. The sequences represented by each of these GenBank accession numbers in incorporated by reference for all purposes.

C/EBPβ or C/EBPb. The protein encoded by this intronless gene is a bZIP transcription factor which can bind as a homodimer to certain DNA regulatory regions. It can also form heterodimers with the related proteins CEBP-alpha, CEBP-delta, and CEBP-gamma. The encoded protein is important in the regulation of genes involved in immune and inflammatory responses and has been shown to bind to the IL-1 response element in the IL-6 gene, as well as to regulatory regions of several acute-phase and cytokine genes. In addition, the encoded protein can bind the promoter and upstream element and stimulate the expression of the collagen type I gene. C/EPB-β is an important transcriptional activator in the regulation of genes involved in immune and inflammatory responses and can work coordinately with inflammation-related transcription factor NFκB. C/EPB-β specifically binds to an IL-1 response element in the IL-6 gene. NF-IL6 also binds to regulatory regions of several acute-phase and cytokines genes. C/EPB-β therefore plays a role in the regulation of acute-phase reaction, inflammation and hemopoiesis. The consensus recognition site is 5'-T[TG]NNGNAA[TG]-3'. C/EPB-β functions in brown adipose tissue (BAT) differentiation. C/EPB-β is located in the nucleus and expressed at low levels in the lung, kidney and spleen. The following GenBank DNA accession numbers represent the C/EBPβ protein sequence: P17676.2, NP_005185.2, AAH05132.2, AAH21931.1, and AAH07538.1. The sequences represented by each of these GenBank accession numbers in incorporated by reference for all purposes.

HLA-DR is a MHC class II cell surface receptor encoded by the human leukocyte antigen complex. The following GenBank DNA accession numbers represent the HLA-DR protein sequence: CAA23788.1, AAA58655.1, and AAO49820.1. The sequences represented by each of these GenBank accession numbers in incorporated by reference for all purposes.

In some embodiments, the detection agent can be an antibody. Antibodies may be prepared using an intact polypeptide or fragments containing smaller polypeptides as the immunizing antigen. For example, it may be desirable to produce antibodies that specifically bind to the N- or C-terminal or any other suitable domains of a protein. The polypeptide used to immunize an animal can be derived from translated cDNA or chemical synthesis and can be conjugated to a carrier protein, if desired. Such commonly used carriers which are chemically coupled to the polypeptide include keyhole limpet hemocyanin (KLH), thyroglobulin, bovine serum albumin (BSA) and tetanus toxoid. The coupled polypeptide is then used to immunize the animal.

If desired, polyclonal or monoclonal antibodies can be further purified, for example by binding to and elution from a matrix to which the polypeptide or a peptide to which the antibodies were raised is bound. Those skilled in the art know various techniques common in immunology for purification and/or concentration of polyclonal as well as monoclonal antibodies (Coligan et al, Unit 9, Current Protocols in Immunology, Wiley Interscience, 1994).

Methods for making antibodies of all types, including fragments, are known in the art (See for example, Harlow and Lane, Antibodies: A Laboratory Manual, Cold Spring Harbor Laboratory, New York (1988)). Methods of immunization, including all necessary steps of preparing the immunogen in a suitable adjuvant, determining antibody binding, isolation of antibodies, methods for obtaining monoclonal antibodies are all known to the skilled artisan The monoclonal antibodies as defined include antibodies derived from one species (such as murine, rabbit, goat, rat, human, etc.) as well as antibodies derived from two (or more) species, such as chimeric and humanized antibodies. Movahedi et al., Blood vol. 111 no. 8 (2008) 4233-44 provides commercial source identification of antibodies to CD11 b, (BD Biosciences) and provides various markers for MDSC by flow cytometry. Other commercially available antibodies include monoclonal antibody to CD33 (PE-Cy™7) (BD Biosciences, Catalog Number 333946), monoclonal antibody to HIF-1α (BD Biosciences, Catalog Number 610958, monoclonal antibody to C/EBPβ (Thermo Scientific Pierce Antibodies, Catalog Number MA1-826 (MA1-826 detects C/EBPβ protein in human, mouse, and rat samples. MA1-826 only detects the LAP* isoform of C/EBPβ).

Some embodiments disclosed herein concern diagnostic and prognostic methods for the detection of inflammation and/or cancer. Such detection methods may be used, for example, for early diagnosis of the disease, to determine whether a tumor is malignant or benign, to monitor the progress of the disease or the progress of treatment protocols, or to assess the grade of the cancer. The detection can occur in vitro or in vivo. The presence of a cancer is determined when the percentage of myeloid cells is at least 2% MDSC, at least 3% MDSC, at least 4% MDSC, at least 5% MDSC, at least 6% MDSC, at least 7% MDSC, at least 8% MDSC, at least 9% MDSC, at least 10% MDSC, at least 11% MDSC, at least 12% MDSC, at least 13% MDSC, at least 14% MDSC, or at least 15% MDSC. Useful methods include, but are not limited to, flow cytometry, an enzyme immune assay (EIA) such as enzyme-linked immunosorbent assay (ELISA), a radioimmunoassay, or Western blot detection.

The methods disclosed herein are applicable to any cancer. Cancers include, but are not limited to HNSCC, breast cancer, cervical cancer, ovarian cancer, colorectal carcinoma, brain cancer, melanoma, sarcoma, endometrial cancer, bladder cancer, renal cancer, gastric cancer, thyroid cancer, small cell lung cancer, non-small cell lung cancer, prostate cancer, liver cancer, and pancreatic cancer.

Cancers can also include malignant lymphoma. Malignant lymphomas can include mature cell neoplasm, mature T cell or natural killer cell neoplasm, and Hodgkins lymphoma.

A tumor is literally a swelling of any type, such as an inflammatory or other swelling, but modem usage generally denotes a neoplasm. The suffix "-oma" means tumor and usually denotes a benign neoplasm, as in fibroma, lipoma, and so forth, but sometimes implies a malignant neoplasm, as with so-called melanoma, hepatoma, and seminoma, or even a non-neoplastic lesion, such as a hematoma, granuloma, or hamartoma. The suffix "-blastoma" denotes a neoplasm of embryonic cells, such as neuroblastoma of the adrenal or retinoblastoma of the eye.

Histogenesis is the origin of a tissue and is a method of classifying neoplasms on the basis of the tissue cell of origin. Adenomas are benign neoplasms of glandular epithelium. Carcinomas are malignant tumors of epithelium. Sarcomas are malignant tumors of mesenchymal tissues. One system to classify neoplasia utilizes biological (clinical) behavior, whether benign or malignant, and the histogenesis, the tissue or cell of origin of the neoplasm as determined by histologic and cytologic examination. Neoplasms may originate in almost any tissue containing cells capable of mitotic division. The histogenetic classification of neoplasms is based upon the tissue (or cell) of origin as determined by histologic and cytologic examination.

"Suppressing" tumor growth indicates a growth state that is curtailed compared to growth without any therapy. Tumor cell growth can be assessed by any means known in the art, including, but not limited to, measuring tumor size, determining whether tumor cells are proliferating using a $^3$H-thymidine incorporation assay, or counting tumor cells. "Suppressing" tumor cell growth means any or all of the following states: slowing, delaying, and "suppressing" tumor growth indicates a growth state that is curtailed when stopping tumor growth, as well as tumor shrinkage.

The term "culturing" refers to the in vitro propagation of cells or organisms on or in media of various kinds. It is understood that the descendants of a cell grown in culture may not be completely identical (morphologically, genetically, or phenotypically) to the parent cell. By "expanded" is meant any proliferation or division of cells.

Mature cell neoplasm can include Chronic lymphocytic leukemia/Small lymphocytic lymphoma, B-cell prolymphocytic leukemia, Lymphoplasmacytic lymphoma (such as Waldenström macroglobulinemia), Splenic marginal zone lymphoma, Plasma cell myeloma, Plasmacytoma, Monoclonal immunoglobulin deposition diseases, Heavy chain diseases, Extranodal marginal zone B cell lymphoma (MALT lymphoma), Nodal marginal zone B cell lymphoma (NMZL), Follicular lymphoma, Mantle cell lymphoma, Diffuse large B cell lymphoma, Mediastinal (thymic) large B cell lymphoma, Intravascular large B cell lymphoma, Primary effusion lymphoma, and Burkitt lymphoma/leukemia.

Mature T or natural killer cell neoplasm can include T cell large granular lymphocytic leukemia, Aggressive NK cell leukemia, Adult T cell leukemia/lymphoma, Extranodal NK/T cell lymphoma (nasal type), Enteropathy-type T cell lymphoma, Hepatosplenic T cell lymphoma, Blastic NK cell lymphoma, Mycosis fungoides/Sezary syndrome, Primary cutaneous CD30-positive T cell lymphoproliferative disorder, Primary cutaneous anaplastic large cell lymphoma, Lymphomatoid papulosis, Angioimmunoblastic T cell lymphoma, Peripheral T cell lymphoma (unspecified), and Anaplastic large cell lymphoma.

The sample can be peripheral blood or any other source of myeloid lineage cells, including, but not limited to, peripheral blood leukocytes, red blood cell lysate of whole peripheral blood, tumor, lymph, lymph node tissue, spleen cells, cerebrospinal fluid, ascities, and pleural effusions. The sample can be fresh, previously frozen, or preserved.

Provided herein are also methods for inducing human MDSC from healthy donor peripheral blood mononuclear cells (PBMC) by co-culturing PBMC with human solid tumor cell lines and subsequently measuring their suppressive ability. Culture methods are well-known in the art. These co-culturing methods generate purified human MDSC in quantities sufficient for morphology, phenotype, gene expression, and functional studies and pre-clinical testing of MDSC inhibitors.

In certain embodiments, provided herein are methods for generating a tumor cell line-educated-$CD33^+$ human MDSC, $CD14^+$ human MDSC, $CD66b^+$ human MDSC, or $CD11b^+$ human MDSC by a) contacting peripheral blood mononuclear cells (PBMCs) with tumor cells, and b) isolating $CD33^+$ cells, $CD14^+$ cells, $CD66b^+$ cells, or $CD11b^+$ human MDSC, respectively. PBMC-tumor cell line co-cultures are established in tissue culture flasks. The tumor can be any solid tumor or malignant lymphoma listed above. Tumor-educated $CD33^+$, $CD14^+$ cells, $CD66b^+$ cells, or $CD11b^+$ cells are isolated from established PBMC-tumor cell line co-cultures. The tumor-educated $CD33^+$, $CD14^+$ cells, $CD66b^+$ cells, or $CD11b^+$ cells can be checked for viability and can be tested for suppressive function by co-culture with fresh, autologous $CD8^+$ T cells in the presence of T cell stimuli. Methods for detecting viability and suppressive function are well-known in the art. The method of generating in vitro human MDSC disclosed herein can be used to generate human MDSC standards and control myeloid cells (such as by culture of PBMC alone or with non-induced tumor or fibroblast cell lines) for use in diagnostic assays and kits thereof.

Also provided herein are methods for identifying a candidate compound as a suppression agonist by comparing suppression activity function of tumor cell line-educated-$CD33^+$ cells, $CD14^+$ cells, $CD66b^+$ cells, or $CD11b^+$ human MDSC in the presence and in the absence of the candidate compound, wherein the relative reduction of T cell proliferation in the presence of the candidate compound indicates pro-suppressive activity.

Further provided is a method for identifying a candidate compound as a suppression antagonist comprising comparing suppression activity function of tumor cell line-educated-$CD33^+$ cells, $CD14^+$ cells, $CD66b^+$ cells, or $CD11b^+$ human MDSC in the presence and in the absence of said candidate compound, wherein the relative increase of T cell proliferation in the presence of said candidate compound indicates anti-suppressive activity.

Also provided herein are methods for treating a subject with cancer by evaluating a cell containing sample from the subject for the presence of myeloid-derived suppressor cells (MDSC), the MDSC being identified by their phenotype of any of $CD33^+HLA\text{-}DR^{low}HIF1\alpha^+/STAT3^+$, $CD14^+HLA\text{-}DR^{low}HIF1\alpha^+/STAT3^+/pSTAT3^+/C/EBPb^+$, $CD66b^+HLA\text{-}DR^{low}HIF1\alpha^+/STAT3^+/pSTAT3^+/C/EBPb^+$, $CD33^+HLA\text{-}DR^{low}HIF1\alpha^+/STAT3^+/pSTAT3^+/C/EBPb^+$, $CD11b^+HLA\text{-}DR^{low}HIF1\alpha^+/STAT3^+/pSTAT3^+/C/EBPb^+$, and $CD11b^+HLA\text{-}DR^{low}C/EBP\beta^+$ and if any of these phenotypes of MDSC is present, administering a cancer therapeutic. In addition, the success of the cancer treatment can be monitored by monitoring the increase or decrease of $CD33^+HLA\text{-}DR^{low}HIF1\alpha^+/STAT3^{++}$, $CD14^+HLA\text{-}DR^{low}HIF1\alpha^+/STAT3^+/pSTAT3^+/C/EBPb^+$, $CD66b^+HLA\text{-}DR^{low}HIF1\alpha^+/STAT3^+/pSTAT3^+/C/EBPb^+$, $CD33^+HLA\text{-}DR^{low}HIF1\alpha^+/STAT3^+/pSTAT3^+/C/EBPb^+$, $CD11b^+HLA\text{-}DR^{low}HIF1\alpha^+/STAT3^+/pSTAT3^+/C/EBPb^+$, or $CD11b^+HLA\text{-}DR^{low}C/EBP\beta^+$ after initiation of therapy.

Cancer therapeutics are known in the art and depend on the cancer being treated. Cancer therapeutics include any treatment regimine typical for the cancer type. Typical cancer therapeutics include radiation therapy, chemotherapy, surgery, and transplantation. It is within the skill of an attending doctor to select the appropriate cancer treatment regimine depending on the specific condition of the subject.

Suitable therapeutic agents include, but are not limited to chemotherapeutic compounds such as DNA alkylating agents, topoisomerase inhibitors, endoplasmic reticulum stress inducing agents, a platinum compound, an antimetabolite, vincalkaloids, taxanes, epothilones, enzyme inhibitors, receptor antagonists, therapeutic antibodies, tyrosine kinase inhibitors, antibiotics, boron radiosensitizers (i.e. velcade) and chemotherapeutic combination therapies. Non-limiting examples of chemotherapeutic agents and therapeutic agents are provided here. Chemical and biological equivalents of these agents are within the scope of this invention.

In one aspect of the invention, the anticancer drug is a DNA alkylating agent which attaches an alkyl group to DNA. Such agents are well known in the art and are used to treat a variety of tumors. Non-limiting examples of a DNA alkylating agents are Nitrogen mustards, such as Mechlorethamine, Cyclophosphamide (Ifosfamide, Trofosfamide), Chlorambucil (Melphalan, Prednimustine), Bendamustine, Uramustine and Estramustine; Nitrosoureas, such as Carmustine (BCNU), Lomustine (Semustine), Fotemustine, Nimustine, Ranimustine and Streptozocin; Alkyl sulfonates, such as Busulfan (Mannosulfan, Treosulfan); Aziridines, such as Carboquone, ThioTEPA, Triaziquone, Triethylenemelamine; Hydrazines (Procarbazine); Triazenes such as Dacarbazine and Temozolomide; Altretamine and Mitobronitol.

In another aspect of the invention, the anticancer drug is a platinum based compound which is a subclass of DNA alkylating agents. Such agents are well known in the art and are used to treat a variety of cancers, such as, lung cancers, head and neck cancers, ovarian cancers, colorectal cancer and prostate cancer. Non-limiting examples of such agents include Carboplatin, Cisplatin, Nedaplatin, Oxaliplatin, Triplatin tetranitrate, Satraplatin, Aroplatin, Lobaplatin, and JM-216. (see McKeage et al. (1997) J. Clin. Oncol. 201:1232-1237 and in general, CHEMOTHERAPY FOR GYNECOLOGICAL NEOPLASM, CURRENT THERAPY AND NOVEL APPROACHES, in the Series Basic and Clinical Oncology, Angioli et al. Eds., 2004).

"Oxaliplatin" (Eloxatin®) is a platinum-based chemotherapy drug in the same family as cisplatin and carboplatin. It is typically administered in combination with fluorouracil and leucovorin in a combination known as FOLFOX for the treatment of colorectal cancer. Compared to cisplatin the two amine groups are replaced by cyclohexyldiamine for improved antitumour activity. The chlorine ligands are replaced by the oxalato bidentate derived from oxalic acid in order to improve water solubility. Equivalents to Oxaliplatin are known in the art and include without limitation cisplatin, carboplatin, aroplatin, lobaplatin, nedaplatin, and JM-216 (see McKeage et al. (1997) J. Clin. Oncol. 201:1232-1237 and in general, CHEMOTHERAPY FOR GYNECOLOGICAL NEOPLASM, CURRENT THERAPY AND NOVEL APPROACHES, in the Series Basic and Clinical Oncology, Angioli et al. Eds., 2004).

In one aspect of the invention, the anticancer drug is a topoisomerase inhibitor which is an agent that interferes with the action of topoisomerase enzymes (topoisomerase I and II). Topoisomerases are enzymes that control the changes in DNA structure by catalyzing the breaking and rejoining of the phosphodiester backbone of DNA. Such agents are well known in the art. Non-limiting examples of Topoisomerase I inhibitors include Campothecine derivatives including CPT-11/Irinotecan, SN-38, APC, NPC, camptothecin, topotecan, exatecan mesylate, 9-nitrocamptothecin, 9-am inocamptothecin, lurtotecan, rubitecan, silatecan, gimatecan, diflomotecan, extatecan, BN-80927, DX-8951f, and MAG-CPT as described in Pommier (2006) Nat. Rev. Cancer 6(10):789-802 and U.S. Patent Appl. No. 2005/0250854; Protoberberine alkaloids and derivatives thereof including berberrubine and coralyne as described in Li et al. (2000) Biochemistry 39(24): 7107-7116 and Gatto et al. (1996) Cancer Res. 15(12):2795-2800; Phenanthroline derivatives including Benzo[i]phenanthridine, Nitidine, and fagaronine as described in Makhey et al. (2003) Bioorg. Med. Chem. 11(8):1809-1820; Terbenzimidazole and derivatives thereof as described in Xu (1998) Biochemistry 37(10):3558-3566; and Anthracycline derivatives including Doxorubicin, Daunorubicin, and Mitoxantrone as described in Foglesong et al. (1992) Cancer Chemother. Pharmacol. 30(2):123-125, Crow et al. (1994) J. Med. Chem. 37(19):3191-3194, and (Crespi et al. (1986) Biochem. Biophys. Res. Commun. 136(2):521-8.

In one aspect of the invention, the topoisomerase I inhibitors can be selected from the group of, but not limited to, Campothecine derivatives including CPT-11/Irinotecan, SN-38, APC, NPC, camptothecin, topotecan, exatecan mesylate, 9-nitrocamptothecin, 9-aminocamptothecin, lurtotecan, rubitecan, silatecan, gimatecan, diflomotecan, extatecan, BN-80927, DX-8951f, and MAG-CPT as described in Pommier (2006) Nat. Rev. Cancer 6(10):789-802 and US Patent Appl. No. 2005/0250854; Protoberberine alkaloids and derivatives thereof including berberrubine and coralyne as described in Li et al. (2000) Biochemistry 39(24):7107-7116 and Gatto et al. (1996) Cancer Res. 15(12):2795-2800; Phenanthroline derivatives including Benzo[i]phenanthridine, Nitidine, and fagaronine as described in Makhey et al. (2003) Bioorg. Med. Chem. 11(8):1809-1820; Terbenzimidazole and derivatives thereof as described in Xu (1998) Biochemistry 37(10):3558-3566; and Anthracycline derivatives including Doxorubicin, Daunorubicin, and Mitoxantrone as described in Foglesong et al. (1992) Cancer Chemother. Pharmacol. 30(2):123-125, Crow et al. (1994) J. Med. Chem. 37(19):3191-3194, and (Crespi et al. (1986) Biochem. Biophys. Res. Commun. 136(2):521-8, will be used in combination therapy with antibody based chemotherapy described above to treat patients identified with the appropriate genetic markers.

Irinotecan (CPT-11) is sold under the tradename of Camptosar®. It is a semi-synthetic analogue of the alkaloid camptothecin, which is activated by hydrolysis to SN-38 and targets topoisomerase I. Chemical equivalents are those that inhibit the interaction of topoisomerase I and DNA to form a catalytically active topoisomerase I-DNA complex. Chemical equivalents inhibit cell cycle progression at G2-M phase resulting in the disruption of cell proliferation.

In another aspect, some agents inhibit Topoisomerase II and have DNA intercalation activity such as, but not limited to, Anthracyclines (Aclarubicin, Daunorubicin, Doxorubicin, Epirubicin, Idarubicin, Amrubicin, Pirarubicin, Valrubicin, Zorubicin) and Antracenediones (Mitoxantrone and Pixantrone).

In one aspect of the invention, Topoisomerase II inhibitors include, but are not limited to Etoposide and Teniposide.

In another aspect of the invention, dual topoisomerase I and II inhibitors selected from the group of, but not limited to, Saintopin and other Naphthecenediones, DACA and other Acridine-4-Carboxamindes, Intoplicine and other Benzopyridoindoles, TAS-103 and other 7H-indeno[2,1-c]Quinoline-7-ones, Pyrazoloacridine, XR 11576 and other Benzophenazines, XR 5944 and other Dimeric compounds, and Anthracenyl-amino Acid Conjugates as described in Denny and Baguley (2003) Curr. Top. Med. Chem. 3(3):339-353. In one aspect, they can be used in combination therapy with antibody based chemotherapy described above to treat patients identified with the appropriate genetic markers.

"Lapatinib" (Tykerb®) is an oncolytic dual EGFR and erbB-2 inhibitor. Lapatinib has been investigated as an anti-cancer monotherapy, as well as in combination with trastuzumab, capecitabine, letrozole, paclitaxel and FOLFIRI (irinotecan, 5-fluorouracil and leucovorin), in a number of clinical trials. It is currently in phase III testing for the oral treatment of metastatic breast, head and neck, lung, gastric, renal and bladder cancer.

A chemical equivalent of lapatinib is a small molecule or compound that is a tyrosine kinase inhibitor or alternatively a HER-1 inhibitor or a HER-2 inhibitor. Several TKIs have been found to have effective antitumor activity and have been approved or are in clinical trials. Examples of such include, but are not limited to Zactima (ZD6474), Iressa (gefitinib) and Tarceva (erlotinib), imatinib mesylate (STI571; Gleevec), erlotinib (OSI-1774; Tarceva), canertinib (CI 1033), semaxinib (SU5416), vatalanib (PTK787/ZK222584), sorafenib (BAY 43-9006), sutent (SU11248) and leflunomide (SU101).

A biological equivalent of lapatinib is a peptide, antibody or antibody derivative thereof that is a HER-1 inhibitor and/or a HER-2 inhibitor. Examples of such include but are not limited to the humanized antibody trastuzumab and Herceptin.

In one aspect of the invention, the therapeutic agent is an endoplasmic reticulum stress inducing agent. Examples of such agents include, but are not limited to, Celecoxib, dimethyl-celecoxib and boron radiosensitizers (i.e. valcade (Bortezomib)).

In another aspect of the invention, the anticancer drug is an antimetabolite agent which inhibits the use of a metabolite, i.e. another chemical that is part of normal metabolism. In cancer treatment, antimetabolites interfere with DNA production, thus cell division and growth of the tumor. Non-limiting examples of these agents are Folic acid based, i.e. dihydrofolate reductase inhibitors, such as Aminopterin, Methotrexate and Pemetrexed; thymidylate synthase inhibitors, such as Raltitrexed, Pemetrexed; Purine based, i.e. an adenosine deaminase inhibitor, such as Pentostatin, a thiopurine, such as Thioguanine and Mercaptopurine, a halogenated/ribonucleotide reductase inhibitor, such as Cladribine, Clofarabine, Fludarabine, or a guanine/guanosine: thiopurine, such as Thioguanine; or Pyrimidine based, i.e. cytosine/cytidine: hypomethylating agent, such as Azacitidine and Decitabine, a DNA polymerase inhibitor, such as Cytarabine, a ribonucleotide reductase inhibitor, such as Gemcitabine, or a thymine/thymidine: thymidylate synthase inhibitor, such as a Fluorouracil (5-FU).

Fluorouracil (5-FU) belongs to the family of therapy drugs call pyrimidine based anti-metabolites. 5-FU is transformed into different cytotoxic metabolites that are then incorporated into DNA and RNA thereby inducing cell cycle arrest and apoptosis. It is a pyrimidine analog, which is transformed into different cytotoxic metabolites that are then incorporated into DNA and RNA thereby inducing cell cycle arrest and apoptosis. Chemical equivalents are pyrimidine analogs which result in disruption of DNA replication. Chemical equivalents inhibit cell cycle progression at S phase resulting in the disruption of cell cycle and consequently apoptosis. Equivalents to 5-FU include prodrugs, analogs and derivative thereof such as 5'-deoxy-5-fluorouridine (doxifluroidine), 1-tetrahydrofuranyl-5-fluorouracil (ftorafur), Capecitabine (Xeloda), S-1 (MBMS-247616, consisting of tegafur and two modulators, a 5-chloro-2,4-dihydroxypyridine and potassium oxonate), ralititrexed (tomudex), nolatrexed (Thymitaq, AG337), LY231514 and ZD9331, as described for example in Papamicheal (1999) The Oncologist 4:478-487.

Capecitabine and Tegafur are examples of chemical equivalents of 5-FU. It is a prodrug of (5-FU) that is converted to its active form by the tumor-specific enzyme PynPase following a pathway of three enzymatic steps and two intermediary metabolites, 5'-deoxy-5-fluorocytidine (5'-DFCR) and 5'-deoxy-5-fluorouridine (5'-DFUR). Capecitabine is marketed by Roche under the trade name Xeloda®.

Leucovorin (Folinic acid) is an adjuvant used in cancer therapy. It is used in synergistic combination with 5-FU to improve efficacy of the chemotherapeutic agent. Without being bound by theory, addition of Leucovorin is believed to enhance efficacy of 5-FU by inhibiting thymidylate synthase. It has been used as an antidote to protect normal cells from high doses of the anticancer drug methotrexate and to increase the antitumor effects of fluorouracil (5-FU) and tegafur-uracil. It is also known as citrovorum factor and Wellcovorin. This compound has the chemical designation of L-Glutamic acid N[4[[(2-amino-5-formyl1,4,5,6,7,8hexahydro4oxo6-pteridinyl)methyl]amino]benzoyl]-, calcium salt (1:1).

Examples of vincalkaloids, include, but are not limited to vinblastine, Vincristine, Vinflunine, Vindesine and Vinorelbine.

Examples of taxanes include, but are not limited to docetaxel, Larotaxel, Ortataxel, Paclitaxel and Tesetaxel. An example of an epothilone is iabepilone.

Examples of enzyme inhibitors include, but are not limited to farnesyltransferase inhibitors (Tipifarnib); CDK inhibitor (Alvocidib, Seliciclib); Proteasome inhibitor (Bortezomib); Phosphodiesterase inhibitor (Anagrelide); IMP dehydrogenase inhibitor (Tiazofurine); and Lipoxygenase inhibitor (Masoprocol).

Examples of tyrosine kinase inhibitors include, but are not limited to ErbB: HER1/EGFR (Erlotinib, Gefitinib, Lapatinib, Vandetanib, Sunitinib, Neratinib); HER2/neu (Lapatinib, Neratinib); RTK class III: C-kit (Axitinib, Sunitinib, Sorafenib); FLT3 (Lestaurtinib); PDGFR (Axitinib, Sunitinib, Sorafenib); and VEGFR (Vandetanib, Semaxanib, Cediranib, Axitinib, Sorafenib); bcr-abl (Imatinib, Nilotinib, Dasatinib); Src (Bosutinib) and Janus kinase 2 (Lestaurtinib).

PTK/ZK is a "small" molecule tyrosine kinase inhibitor with broad specificity that targets all VEGF receptors (VEGFR), the platelet-derived growth factor (PDGF) receptor, c-KIT and c-Fms. Drevs (2003) Idrugs 6(8):787-794. PTK/ZK is a targeted drug that blocks angiogenesis and lymphangiogenesis by inhibiting the activity of all known receptors that bind VEGF including VEGFR-1 (Flt-1), VEGFR-2 (KDR/Flk-1) and VEGFR-3 (Flt-4). The chemical names of PTK/ZK are 1-[4-Chloroanilino]-4-[4-pyridylmethyl]phthalazine Succinate or 1-Phthalazinamine, N-(4-chlorophenyl)-4-(4-pyridinylmethyl)-, butanedioate (1:1). Synonyms and analogs of PTK/ZK are known as Vatalanib, CGP79787D, PTK787/ZK 222584, CGP-79787, DE-00268, PTK-787, PTK-787A, VEGFR-TK inhibitor, ZK 222584 and ZK.

Examples of chemotherapeutic agents and combination therapies include, but are not limited to amsacrine, Trabectedin, retinoids (Alitretinoin, Tretinoin), Arsenic trioxide, asparagine depleter (Asparaginase/Pegaspargase), Celecoxib, Demecolcine, Elesclomol, Elsamitrucin, Etoglucid, Lonidamine, Lucanthone, Mitoguazone, Mitotane, Oblimersen, Temsirolimus, and Vorinostat.

"FOLFOX" is an abbreviation for a type of combination therapy that is used to treat colorectal cancer. It includes 5-FU, oxaliplatin and leucovorin. Information regarding this treatment is available on the National Cancer Institute's web site, cancer.gov, last accessed on Jan. 16, 2008.

"FOLFOX/BV" is an abbreviation for a type of combination therapy that is used to treat colorectal cancer. This therapy includes 5-FU, oxaliplatin, leucovorin and Bevacizumab. Furthermore, "XELOX/BV" is another combination therapy used to treat colorectal cancer, which includes the prodrug to 5-FU, known as Capecitabine (Xeloda) in combination with oxaliplatin and bevacizumab. Information regarding these treatments are available on the National Cancer Institute's web site, cancer.gov or from the National Comprehensive Cancer Network's web site, nccn.org, last accessed on May 27, 2008.

Examples of therapeutic antibodies include, but are not limited to anti-HER1/EGFR (Cetuximab, Panitumumab); Anti-HER2/neu (erbB2) receptor (Trastuzumab); Anti-Ep-CAM (Catumaxomab, Edrecolomab) Anti-VEGF-A (Bevacizumab); Anti-CD20 (Rituximab, Tositumomab, Ibritumomab); Anti-CD52 (Alemtuzumab); and Anti-CD33 (Gemtuzumab), as well as biological equivalents thereof.

Bevacizumab is sold under the trade name Avastin by Genentech. It is a humanized monoclonal antibody that binds to and inhibits the biologic activity of human vascular endothelial growth factor (VEGF). Biological equivalent antibodies are identified herein as modified antibodies and those which bind to the same epitope of the antigen, prevent the interaction of VEGF to its receptors (Flt01, KDR a.k.a. VEGFR2) and produce a substantially equivalent response, e.g., the blocking of endothelial cell proliferation and angiogenesis.

In one aspect, the "chemical equivalent" means the ability of the chemical to selectively interact with its target protein, DNA, RNA or fragment thereof as measured by the inactivation of the target protein, incorporation of the chemical into the DNA or RNA or other suitable methods. Chemical equivalents include, but are not limited to, those agents with the same or similar biological activity and include, without limitation a pharmaceutically acceptable salt or mixtures thereof that interact with and/or inactivate the same target protein, DNA, or RNA as the reference chemical.

In one aspect, the "biological equivalent" means the ability of the antibody to selectively bind its epitope protein or fragment thereof as measured by ELISA or other suitable methods. Biologically equivalent antibodies include, but are not limited to, those antibodies, peptides, antibody fragments, antibody variant, antibody derivative and antibody mimetics that bind to the same epitope as the reference antibody. An example of an equivalent Bevacizumab antibody is one which binds to and inhibits the biologic activity of human vascular endothelial growth factor (VEGF).

Formulations

The pharmaceutical compositions can be administered by any one of the following routes: ocular, oral, systemic (e.g., transdermal, intranasal or by suppository), or parenteral (e.g., intramuscular, intravenous or subcutaneous) administration. In some embodiments, the manner of administration is oral using a convenient daily dosage regimen that can be adjusted according to the degree of affliction. Compositions can take the form of tablets, pills, capsules, semisolids, powders, sustained release formulations, solutions, suspensions, elixirs, aerosols, or any other appropriate compositions. Another manner for administering compounds of described herein is inhalation.

The choice of formulation depends on various factors such as the mode of drug administration and bioavailability of the drug substance. For delivery via inhalation the compound can be formulated as liquid solution, suspensions, aerosol propellants or dry powder and loaded into a suitable dispenser for administration. There are several types of pharmaceutical inhalation devices-nebulizer inhalers, metered dose inhalers (MDI), mouth mask and dry powder inhalers (DPI). Nebulizer devices produce a stream of high velocity air that causes the therapeutic agents (which are formulated in a liquid form) to spray as a mist that is carried into the patient's respiratory tract. MDI's typically are formulation packaged with a compressed gas. Upon actuation, the device discharges a measured amount of therapeutic agent by compressed gas, thus affording a reliable method of administering a set amount of agent. DPI can dispense therapeutic agents in the form of a free flowing powder that can be dispersed in the patient's inspiratory air-stream during breathing by the device. In order to achieve a free flowing powder, the therapeutic agent is formulated with an excipient such as lactose. A measured amount of the therapeutic agent is stored in a capsule form and is dispensed with each actuation.

Recently, pharmaceutical formulations have been developed especially for drugs that show poor bioavailability based upon the principle that bioavailability can be increased by increasing the surface area i.e., decreasing particle size. For example, U.S. Pat. No. 4,107,288 describes a pharmaceutical formulation having particles in the size range from 10 to 1,000 nm in which the active material is supported on a crosslinked matrix of macromolecules. U.S. Pat. No. 5,145,684 describes the production of a pharmaceutical formulation in which the drug substance is pulverized to nanoparticles (average particle size of 400 nm) in the presence of a surface modifier and then dispersed in a liquid medium to give a pharmaceutical formulation that exhibits remarkably high bioavailability.

For ocular administration, the compositions described herein can be formulated as a solution, emulsion, suspension, etc., suitable for administration to the eye. A variety of vehicles suitable for administering compounds to the eye are known in the art. Specific non-limiting examples are described in U.S. Pat. No. 6,261,547; U.S. Pat. No. 6,197, 934; U.S. Pat. No. 6,056,950; U.S. Pat. No. 5,800,807; U.S. Pat. No. 5,776,445; U.S. Pat. No. 5,698,219; U.S. Pat. No. 5,521,222; U.S. Pat. No. 5,403,841; U.S. Pat. No. 5,077,033; U.S. Pat. No. 4,882,150; and U.S. Pat. No. 4,738,851.

The compositions can additional contain solid pharmaceutical excipients such as starch, cellulose, talc, glucose, lactose, sucrose, gelatin, malt, rice, flour, chalk, silica gel, magnesium stearate, sodium stearate, glycerol monostearate, sodium chloride, dried skim milk and the like. Liquid and semisolid excipients may be selected from glycerol, propylene glycol, water, ethanol and various oils, including those of petroleum, animal, vegetable or synthetic origin, e.g., peanut oil, soybean oil, mineral oil, sesame oil, etc. Liquid carriers, particularly for injectable solutions, include water, saline, aqueous dextrose, and glycols.

Compressed gases may be used to disperse a composition described herein in aerosol form. Inert gases suitable for this purpose are nitrogen, carbon dioxide, etc. Other suitable pharmaceutical excipients and their formulations are described in Remington's Pharmaceutical Sciences, edited by E. W. Martin (Mack Publishing Company, 18th ed., 1990).

The amount of the composition in a formulation can vary within the full range employed by those skilled in the art. Typically, the formulation will contain, on a volume percent (v/v %) basis, from about 0.01-99.99 v/v % of a composition described herein based on the total formulation, with the balance being one or more suitable pharmaceutical excipients. In some embodiments, the composition is present at a level of about 1-80 v/v %.

Thus, the composition of this invention can be formulated for administration intranasally as a spray or in a drop; transdermally via a transdermal patch or iontorphoresis and by inhalation using a nebulizer, MDI or similar device. As such, the compositions can further comprise, or alternatively consist essentially of, or yet further consist of, a permeation or penetration enhancer, a plasticizer, or the like making the composition suitable for transdermal administration. In one aspect, the invention is a transdermal reservoir having within it an effective amount of a composition of this invention for transdermal administration of the composition. In a further aspect, the invention provides a transdermal device containing the transdermal reservoir. The transdermal reservoir and/or device can be used to administer an effective amount of the composition of this invention to a subject in need of treatment. These devices are suitable to administer pain medications such as analgesics and narcotics. Examples of these therapeutic agents are provided supra.

This invention also provides the compositions as described above for intranasal administration. As such, the compositions can further comprise, or alternatively consist essentially of, or yet further consist of, a permeation or penetration enhancer or the like making the composition suitable for intranasal administration. In one aspect, the invention is an intranasal formulation having within it an effective amount of a composition of this invention for intranasal administration of the composition. These formulations are suitable to cancer drugs or drugs to treat neurological disorders. Examples of these drugs are provided below.

This invention also provides the compositions as described above for administration by inhalation. As such, the compositions can further comprise, or alternatively consist essentially of, or yet further consist of, a permeation or penetration enhancer or the like making the composition suitable for administration by inhalation. In one aspect, the invention is formulation for administration by inhalation having within it an effective amount of a composition of this invention for inhalation of the composition. These formulations are suitable to administer cancer drugs or drugs to treat neurological disorders. Examples of these drugs are provided supra.

When practiced in vivo in a subject other than a human patient such as a mouse, the method provides an animal model for use in discovering alternative agents, compositions and therapies. In a human patient, the method treats pathologies as described above or as characterized by hyperproliferative cells, e.g., cancer. Methods for detecting clinical and sub-clinical evidence of effective therapy are known in the art and described in U.S. Patent Appl. No. 2004/0087651, (published May 6, 2004), Balassiano et al. (2002) Intern. J. Mol. Med. 10:785-788; Thorne et al. (2004) Neuroscience 127:481-496; Fernandes et al. (2005) Oncology Reports 13:943-947; da Fonseca et al. (2006) 66:611-615; da Fonseca et al. (2008) Surgical Neurology 70:259-267; da Fonseca et al. (2008) Arch. Immunol. Ther. Exp. 56:267-276 and Hashizume et al. (2008) Neuroncology 10:112-120, each incorporated by reference. In each of these methods, an effective amount of a composition of this invention is delivered or administered to the subject, e.g., mouse or human patient.

This invention also provides a method for treating a disease in a subject in need of such treatment comprising, or alternatively consisting essentially of, or yet further consisting of, administering to the subject an effective amount of the composition as described herein to the subject, thereby treating the disease.

The compositions can be administered to an animal or mammal by a treating veterinarian.

Also provided herein are methods for determining a prognosis of a subject with cancer by evaluating a cell containing sample from the subject for the presence of myeloid-derived suppressor cells (MDSC), the MDSC being identified by their phenotype of any of CD33$^+$HLA-DR$^{low}$HIF1α$^+$/STAT3$^+$, CD14$^+$HLA-DR$^{low}$HIF1α$^+$/STAT3$^+$/pSTAT3$^+$/C/EBPb$^+$, CD66b$^+$HLA-DR$^{low}$HIF1α$^+$/STAT3$^+$/pSTAT3$^+$/C/EBPb$^+$, CD33$^+$HLA-DR$^{low}$HIF1α$^+$/STAT3$^+$/pSTAT3$^+$/C/EBPb$^+$, CD11b$^+$HLA-DR$^{low}$HIF1α$^+$/STAT3$^+$/pSTAT3$^+$/C/EBPb$^+$, and CD11b$^+$HLA-DR$^{low}$C/EBPβ$^+$ and if any of these phenotypes of MDSC is present, altering treatment. Prognosis includes determining overall survival, early disease recurrence, and treatment failure.

The methods described herein may be performed, for example, by utilizing pre-packaged diagnostic kits, such as those described below, comprising at least one probe or primer nucleic acid described herein, which may be conveniently used, e.g., to determine whether a subject is likely to experience tumor recurrence following therapy as described herein or has or is at risk of developing disease such as colon cancer.

Diagnostic procedures can also be performed in situ directly upon tissue sections (fixed and/or frozen) of primary tissue such as biopsies obtained from biopsies or resections, such that no nucleic acid purification is necessary. Nucleic acid reagents can be used as probes and/or primers for such in situ procedures (see, for example, Nuovo, G. J. (1992) PCR IN SITU HYBRIDIZATION: PROTOCOLS AND APPLICATIONS, RAVEN PRESS, NY).

In addition to methods which focus primarily on the detection of one nucleic acid sequence, profiles can also be assessed in such detection schemes. Fingerprint profiles can be generated, for example, by utilizing a differential display procedure, Northern analysis and/or RT-PCR.

Probes can be affixed to surfaces for use as "gene chips." Such gene chips can be used to detect genetic variations by a number of techniques known to one of skill in the art. In one technique, oligonucleotides are arrayed on a gene chip for determining the DNA sequence of a by the sequencing by hybridization approach, such as that outlined in U.S. Pat. Nos. 6,025,136 and 6,018,041. The probes of the disclosure also can be used for fluorescent detection of a genetic sequence. Such techniques have been described, for example, in U.S. Pat. Nos. 5,968,740 and 5,858,659. A probe also can be affixed to an electrode surface for the electrochemical detection of nucleic acid sequences such as described by Kayem et al. U.S. Pat. No. 5,952,172 and by Kelley et al. (1999) Nucleic Acids Res. 27:4830-4837.

This disclosure also provides for a panel of genetic markers selected from, but not limited to the probes and/or primers to determine gene expression as identified herein. The probes or primers can be attached or supported by a solid phase support such as, but not limited to a gene chip or microarray. The probes or primers can be detectably labeled.

In one aspect, the panel contains the herein identified probes or primers as wells as other probes or primers. In a alternative aspect, the panel includes one or more of the above noted probes or primers and others. In a further aspect, the panel consist only of the above-noted probes or primers.

Primers or probes can be affixed to surfaces for use as "gene chips" or "microarray." Such gene chips or microarrays can be used to detect genetic variations by a number of techniques known to one of skill in the art. In one technique, oligonucleotides are arrayed on a gene chip for determining the DNA sequence of a by the sequencing by hybridization approach, such as that outlined in U.S. Pat. Nos. 6,025,136 and 6,018,041. The probes of the disclosure also can be used for fluorescent detection of a genetic sequence. Such techniques have been described, for example, in U.S. Pat. Nos. 5,968,740 and 5,858,659. A probe also can be affixed to an electrode surface for the electrochemical detection of nucleic acid sequences such as described by Kayem et al. U.S. Pat. No. 5,952,172 and by Kelley et al. (1999) Nucleic Acids Res. 27:4830-4837.

Various "gene chips" or "microarray" and similar technologies are know in the art. Examples of such include, but are not limited to LabCard (ACLARA Bio Sciences Inc.); GeneChip (Affymetric, Inc); LabChip (Caliper Technologies Corp); a low-density array with electrochemical sensing (Clinical Micro Sensors); LabCD System (Gamera Bioscience Corp.); Omni Grid (Gene Machines); Q Array (Genetix Ltd.); a high-throughput, automated mass spectrometry systems with liquid-phase expression technology (Gene Trace Systems, Inc.); a thermal jet spotting system (Hewlett Packard Company); Hyseq HyChip (Hyseq, Inc.); BeadArray (Illumina, Inc.); GEM (Incyte Microarray Systems); a high-throughput microarraying system that can dispense from 12 to 64 spots onto multiple glass slides (Intelligent Bio-Instruments); Molecular Biology Workstation and NanoChip (Nanogen, Inc.); a microfluidic glass chip (Orchid biosciences, Inc.); BioChip Arrayer with four PiezoTip piezoelectric drop-on-demand tips (Packard Instruments, Inc.); FlexJet (Rosetta Inpharmatic, Inc.); MALDI-TOF mass spectrometer (Sequnome); ChipMaker 2 and ChipMaker 3 (TeleChem International, Inc.); and GenoSensor (Vysis, Inc.) as identified and described in Heller (2002) Annu. Rev. Biomed. Eng. 4:129-153. Examples of "Gene chips" or a "microarray" are also described in U.S. Patent Publ. Nos.: 2007/0111322, 2007/0099198, 2007/0084997, 2007/0059769 and 2007/0059765 and U.S. Pat. Nos. 7,138,506, 7,070,740, and 6,989,267.

In one aspect, "gene chips" or "microarrays" containing probes or primers for the gene of interest are provided alone or in combination with other probes and/or primers. A suitable sample is obtained from the patient extraction of genomic DNA, RNA, or any combination thereof and amplified if necessary. The DNA or RNA sample is contacted to the gene chip or microarray panel under conditions suitable for hybridization of the gene(s) of interest to the probe(s) or primer(s) contained on the gene chip or microarray. The probes or primers may be detectably labeled thereby identifying the polymorphism in the gene(s) of interest. Alternatively, a chemical or biological reaction may be used to identify the probes or primers which hybridized with the DNA or RNA of the gene(s) of interest. The genetic profile of the patient is then determined with the aid of the aforementioned apparatus and methods.

EXAMPLES

Materials and Methods

Cell Lines and Cell Culture

Tumor cell lines were obtained from the American Type Culture Collection (ATCC) or gifted to the Epstein laboratory. Tumor cell line authenticity was performed by cytogenetics and surface marker analysis performed at ATCC or in our laboratory. All cell lines were maintained at 37° C. in complete medium [(RPMI-1640 with 10% fetal calf serum (characterized FCS, Hyclone, Inc., Logan, Utah), 2 mM L-Glutamine, 100 U/mL Penicillin, and 100 µg/mL Streptomycin)] in tissue culture flasks in humidified, 5% $CO_2$ incubators and passaged 2-3 times per week by light trypsinization.

Tumor Associated MDSC Generation Protocol i. Induction

Human PBMC were isolated from healthy volunteer donors by venipuncture (60 mL total volume) followed by differential density gradient centrifugation (Ficoll Hypaque, Sigma, St. Louis, Mo.). PBMC were cultured in complete medium ($6 \times 10^5$ cells/mL, supplemented with rhGM-CSF (10 ng/mL, R&D Systems, Minneapolis, Minn.) to support viability) in T-25 culture flasks with human tumor cell lines for one week. Tumor cells were seeded to achieve confluence by day 7 (approximately 1:100 ratio with PBMC), and samples in which tumor cells overgrew were excluded from analysis and were repeated with adjusted ratios. Alternatively, irradiated tumor cells (3500 rad) were initially seeded at 1:10 ratio in co-cultures to examine whether induction was dependent upon actively dividing tumor cells. PBMC cultured in medium alone were run in parallel as an induction negative control for each donor to control for any effects of FCS. For neutralization experiments, PBMC-tumor cell line co-cultures were repeated in the presence or absence of neutralizing monoclonal antibodies for a subset of HNSCC cell lines: anti-VEGF (Avastin, Genetech, San Francisco, Calif.), anti-TNFα (Humira, Abbott, Abbott Park, Ill.), anti-IL-1β (clone AB-206-NA, Abcam, Cambridge, Mass.), anti-IL-6 (clone AB-201-NA, Abcam), or anti-GM-CSF (clone BVD2). $CD33^+$ or $CD11b^+$ cells were subsequently isolated and tested for suppressive function as described below. For these studies 61 healthy volunteer donors (39 male, 22 female) ages 20 to 62 were used under USC Institutional Review Board-approved protocol HS-06-00579. Data were derived from at least two individuals and no inter-donor differences in MDSC induction or function were observed.

ii. MDSC Isolation

After one week, all cells were collected from tumor-PBMC co-cultures. Adherent cells were removed using the non-protease cell detachment solution Detachin (GenLantis, San Diego, Calif.). Myeloid ($CD33^+$) cells were then isolated from the co-cultures using anti-CD33 magnetic microbeads and LS column separation (Miltenyi Biotec, Germany) as per manufacturer's instructions. Purity of isolated cell populations was found to be greater than 90% by flow cytometry and morphological examination. Viability of isolated cells was confirmed using trypan blue dye exclusion and samples with viability less than 80% were excluded from analysis and repeated in subsequent experiments. Yields of CD33+ cells from co-cultures averaged 8.75% of PBMC (range 6-12%), while yields from medium only cultures averaged 10%. For isolation of CD11b+ suppressor cells from breast carcinoma co-cultures, anti-CD11b microbeads were used instead of anti-CD33 microbeads.

iii. Suppression Assay

The suppressive function of tumor-educated CD33+ or CD11b+ cells was measured by their ability to inhibit the proliferation of autologous T cells in the following Suppression Assay: CD8+ T cells isolated from 30 mL of PBMC from returning healthy donors were CFSE-labeled (3 µM, Sigma) and seeded in 96-well plates at $2 \times 10^5$ cells/well. CD33+ cells isolated previously (ii. MDSC isolation, above) were added to the 96-well plates at a ratio of 1:4 relative to the T cells. T cell stimulation was provided by anti-CD3/CD28 stimulation beads (Invitrogen, Carlsbad, Calif.). Suppression Assay wells were analyzed by flow cytometry for T cell proliferation after three days and supernatants were analyzed for IFNγ levels (below). Controls included a positive T cell proliferation control (T cells alone) and an induction negative control of CD33+ or CD11b+ cells isolated from PBMC cultured in medium only. Samples were run in duplicate and data were collected as percent proliferation for 15,000 cells. Samples were run on a FACSCalibur flow cytometer (BD Biosciences, San Jose, Calif.) and data acquisition and analysis were performed using CellQuestPro software (BD) at the USC Flow Cytometry core facility.

Characterization of Myeloid Suppressor Cells i. Morphology of MDSC

Wright-Giemsa staining (Protocol Hema 3, Fisher, Kalamazoo, Mich.) of CD33+ or CD11b+ cell cytospin preparations was performed to assess the morphology of tumor-educated myeloid cells. Freshly isolated PBMC and CD33+ (or CD11b+) cultured in medium only or induced by cytokines GM-CSF+IL-6 (26) were prepared in parallel for comparison. Observation, evaluation, and image acquisition were performed using a Leica DM2500 microscope (Leica Microsystems, www.leica-microsystems.com) connected to an automated, digital SPOT RTke camera and SPOT Advanced Software (SPOT Diagnostic Instrument Inc., www.diaginc.com). Images were resized, brightened, and adjusted for color for publication using Adobe Photoshop software (Adobe, www.adobe.com).

ii. Flow Cytometry Analyses of Cell Phenotypes

The phenotype of in vitro-generated MDSC was examined for expression of myeloid, antigen-presenting, and suppressor cell markers and compared to non-suppressive tumor-educated CD33+ or CD11b+ cells. For staining, cells were collected from flasks using Detachin to minimize cell surface protein digestion, and washed twice with FACS buffer (2% FCS in PBS) before resuspending $10^6$ cells in 100 µl FACS buffer. Cells were stained for 1 hr on ice with cocktails of fluorescently-conjugated monoclonal antibodies or isotype-matched controls, washed twice with FACS buffer, and resuspended in FACS buffer for analysis. For intracellular staining, cells were fixed and permeabilized using Fixation/Permeabilization Kit (eBioscience, San Diego, Calif.) after surface staining. Antibodies used were purchased either from BD Biosciences: CD11c (B-ly6), CD33 (HIM3-4), HLA-DR (L243), CD11b (ICRF44), CD66b (G10F5), CD14 (M5E2), CD68 (Y1/82A), 41 BBL (C65-485), OX4OL (Ik-1); or eBioscience (San Diego, Calif.): CD30 (Ber-H2), CD103 (B-Ly7), GITRL (eBioAITR-L), CD56 (MEM-188). Samples were run on a BD FACSCalibur flow cytometer and data acquisition and analysis were performed as above. Data are shown from three unique donors and expressed as a fraction of labeled cells within a live-cell gate set for 15,000 events. CD33+ or CD11b+ cells from PBMC cultured in medium alone were run in parallel for comparison.

iii. Real-Time RT-PCR for Gene Expression of Myeloid Suppressor Cells and Tumor Cell Lines For gene expression studies, tumor-educated CD33+ or CD11b+ cells were isolated from tumor-PBMC co-cultures by fluorescence activated cell sorting after induction (i. Induction, above) and RNA was isolated from MDSC and DNase-treated using Qiagen's RNeasy micro kit (Valencia, Calif.). RNA was isolated from cultured tumor cells and DNase-treated using Qiagen RNeasy mini kit. For real-time RT-PCR, 100 ng of DNase-treated RNA was amplified with gene specific primers using one-step Power SYBR green RNA-to-Ct kit (Applied Biosystems) and run in an MX3000P Strategene thermocycler (La Jolla, Calif.). Data were acquired and analyzed using MxPro software (Stratagene). Gene expression was normalized to housekeeping gene GAPDH and fold change determined relative to expression levels in medium only-cultured cells. Primer sequences were obtained from the NIH qRT-PCR database (http://primerdepot.nci.nih.gov) and were synthesized by the USC Core Facility (29).

iv. Immunohistochemistry

Immunohistochemistry studies were performed on cytospin preparations of suppressive and non-suppressive myeloid cells using antibodies against p-STAT3 (clone 6D779, dilution 1:400) and C/EBPβ (clone H-7, dilution 1:100) (Santa Cruz Biotech).

v. Measurement of Tumor-Derived Factors by ELISA

Supernatants were collected from cell line cultures, passed through a 0.2 µm syringe filter unit to remove cell debris, and stored in aliquots at −20° C. Levels of IL-1β, IL-6, TNFα, VEGF and GM-CSF in supernatant samples were measured using ELISA DuoSet kits (R&D) per manufacturer's instructions. Plate absorbance was read on an ELX-800 plate reader (Bio-Tek, Winooski, Vt.) and analyzed using KC Junior software (Bio-Tek).

vi. Statistical Analysis

Changes in mean T cell proliferation and mean IFNγ production in the presence or absence of tumor-educated MDSC were tested for statistical significance by one-way ANOVA followed by Dunnett test for pairwise comparisons of experimental samples to T cells alone. Changes in mean T cell proliferation in suppression assays in the presence or absence of single inhibitors of suppressive mechanisms were evaluated by ANOVA followed by Tukey's test for pairwise comparisons between all groups. Differences in mean expression of phenotypic markers between pooled groups of suppressive and non-suppressive CD33+ or CD11b+ cells were tested for significance by Student's t test for independent samples. Differences in mean transcription factor or suppressive gene expression between CD11b+ and CD33+ MDSC were tested for significance by Student's t test. Statistical tests were performed using GraphPad Prism software (La Jolla, Calif.) with a significance level of 0.05. Graphs and figures were produced using GraphPad Prism, Microsoft Excel, and Adobe Illustrator and Photoshop software (San Jose, Calif.).

Results

Induction of Tumor-Associated Human Myeloid Suppressor Cells

A protocol for the generation of tumor cell line educated-CD33+ human MDSC from normal donor PBMC was developed (FIG. 1). As provided in detail above, PBMC-tumor cell line co-cultures were established in tissue culture flasks for one week. Tumor-educated CD33+ cells were then isolated, checked for viability, and tested for suppressive function by co-culture with fresh, autologous CD8+ T cells in the presence of T cell stimuli. Controls run for each donor in these studies included T cells with CD33+ from PBMC cultured in medium alone (induction negative control) and T cells alone (proliferation positive control). Use of irradiated tumor cells in co-cultures yielded comparable suppressor cell induction, suggesting that tumor cells need not be actively dividing to mediate the observed induction of suppressive function. Unfractionated PBMC preparations were used in evaluating the ability of human solid tumor cell lines to generate myeloid suppressor cells to best approximate an in vivo setting, but CD33+ suppressor cells were also generated successfully from T cell-depleted PBMC by co-culture with 4-998 osteogenic sarcoma or SCCL-MT1 head and neck squamous cell carcinoma (HNSCC) cells. The same protocol was used for the generation of tumor cell line educated-CD11b+ human MDSC from normal donor PBMC.

Identification of a Subset of Human Tumor Cell Lines with Strong Myeloid Suppressor Cell Induction Capability One-hundred-one human solid tumor cell lines were tested for their ability to induce MDSC using the tumor co-culture assay. MDSC could be generated by at least one cell line of every human tumor type examined (cervical/endometrial, ovarian, pancreatic, lung, head and neck, renal cell, liver, colorectal, prostate, thyroid, gastric, bladder, sarcoma, and glioblastoma), with the exception of breast carcinoma (Tables 1). CD33+ cells from tumor co-cultures were categorized as strong MDSC (ability to suppress autologous T cell proliferation by greater than 50%), weak MDSC (50-20%, meeting statistical significance), or non-suppressive myeloid cells (n≥2 biologic samples). Of 101 tumor cell lines examined, 45 consistently generated MDSC with 30 of those generating strongly suppressive MDSC. A range of suppressor cell ability appeared to exist within histologic types for the majority of tumor cell lines examined, with the notable exception that no human breast cancer cell lines (0/9) tested generated suppressive CD33+ cells.

TABLE 1

| Inducing Tumor Cell Line | Mean Percent Suppression | SEM |
|---|---|---|
| Controls | | |
| T cells alone | 0.00 | |
| Medium only | −2.35 | 0.86 |
| Fetal Lung Fibroblasts | −1.03 | 0.96 |
| Ditt Fibroblasts | −0.13 | 2.91 |
| **GM-CSF + IL-6 | 56.30 | 5.01 |
| HNSCC (6/8) | | |
| **SCCL-MT1 | 91.83 | 0.82 |
| **Irradiated | 89.18 | 0.20 |
| **Tcell Depl. | 81.49 | 4.98 |
| **USC-HN2 | 87.97 | ND |
| **SCC-4 | 65.72 | 2.08 |
| **CAL-27 | 66.26 | 6.21 |
| **SW 451 | 59.49 | 9.59 |
| *FaDu | 30.98 | 4.45 |
| RPMI 2650 | 17.46 | 5.01 |
| SW 2224 | −13.48 | 11.21 |
| Thyroid (1/2) | | |
| **SW 579 | 68.97 | 3.41 |
| SW 1949 | 43.90 | 13.68 |
| Brain (2/9) | | |
| **NU-04 | 69.41 | 4.02 |
| **U118MG | 51.96 | 1.48 |
| SW 598 | 14.29 | 4.14 |
| A172 | 2.26 | 4.97 |
| IMR-5 | −1.23 | 3.09 |
| IMR-32 | −3.16 | 7.48 |
| TE 671 | −12.23 | 4.29 |
| Y79 | −72.63 | 5.58 |
| BM-166 | −83.22 | 0.05 |
| Melanoma (1/3) | | |
| **A375 | 56.16 | 0.64 |
| CaC174-36 | 17.26 | 6.83 |
| Colo 38 | 15.83 | 1.49 |
| Cervical/Endometrial (4/5) | | |
| **HeLa | 68.35 | 5.36 |
| **ME-180 | 75.24 | 3.83 |
| **SIHA | 54.49 | 8.66 |
| **RL95-2 | 52.11 | 3.84 |
| SW 756 | −83.60 | 2.18 |
| Ovarian (6/9) | | |
| **A2780 | 64.46 | 5.33 |
| **ES-2 | 63.62 | 5.17 |
| **TOV-21G | 52.86 | 11.37 |
| **SK-OV-3 | 51.44 | 9.81 |
| *NIHOVCAR-3 | 47.89 | 1.08 |
| *SW 626 | 46.54 | 4.07 |
| HOC-7 | 41.77 | 19.15 |
| HEY | 22.20 | 3.87 |
| Caov-3 | −146.53 | 2.69 |
| Breast (0/9) | | |
| MCF-7 | 16.95 | 0.39 |
| 734B | 16.72 | 2.32 |
| T47D | 8.47 | 1.23 |
| BT-474 | 0.83 | 11.53 |
| SKBR3 | −0.09 | 13.53 |
| MDA-MB-468 | −3.46 | 0.25 |
| GI-101 | −6.41 | 0.92 |
| SV-BR-1 | −8.00 | 1.75 |
| MDA231 | −16.21 | 2.60 |
| Bladder (1/3) | | |
| **T24 | 53.89 | 3.97 |
| SW 780 | 8.10 | 10.01 |
| SW 733 | −54.63 | 0.45 |
| Sarcomas (4/9) | | |
| **4-998 | 58.31 | 0.82 |
| **Irradiated | 52.10 | 0.44 |
| **Tcell Depl | 65.23 | 8.17 |
| *Rh30 | 44.63 | 2.51 |
| *HOS | 42.58 | 4.86 |
| *SW 1353 | 42.22 | 4.42 |
| HT 1080 | 19.37 | 5.92 |
| SA-4 | 12.53 | 1.05 |
| HS919 | 3.01 | 5.31 |
| SW 80 | −5.00 | 3.93 |
| HS 913T | −56.35 | 1.45 |
| Lung Non-small cell (2/7) | | |
| *A427 | 27.71 | 6.87 |
| *SW 1573 | 21.47 | 1.64 |
| H292 | 8.23 | 2.89 |
| NCI-H1650 | 6.67 | 4.18 |
| SK-MES-1 | 4.31 | 6.03 |

TABLE 1-continued

| Inducing Tumor Cell Line | Mean Percent Suppression | SEM |
|---|---|---|
| 125 | 1.54 | 3.69 |
| NCI-H1975 | 0.28 | 2.89 |
| Small Cell (2/3) | | |
| **464 | 63.96 | 6.00 |
| *60 | 47.79 | 7.71 |
| HUT69C | −24.28 | 16.75 |
| Mesothelloma (0/1) | | |
| SW 1503 | 1.93 | 2.02 |
| Liver (2/5) | | |
| *HA 22T | 44.01 | 4.22 |
| *HEP 3B | 23.52 | 7.44 |
| PLC | 22.05 | 5.22 |
| MAH | 11.87 | 4.72 |
| HEP-G2 | −2.10 | 9.40 |
| Renal (3/6) | | |
| **786-O | 75.91 | 6.06 |
| **CAKI-1 | 64.94 | 3.70 |
| **CAKI-2 | 63.62 | 5.17 |
| SW 156 | 36.51 | 10.69 |
| ACHN | 9.85 | 0.20 |
| SK-NEP-1 | 0.00 | 1.82 |
| Prostate (2/3) | | |
| **DU 145 | 54.73 | 2.07 |
| *LNCaP | 29.09 | 2.78 |
| PC3 | 15.12 | 9.09 |
| Gastric (1/2) | | |
| **SW 1961 | 64.55 | 3.04 |
| KATO-III | 7.65 | 2.16 |
| Colorectal (5/6) | | |
| **SW 732 | 69.19 | 1.29 |
| **DLD-1 | 65.59 | 3.19 |
| **SW 608 | 53.11 | 5.15 |
| **SW 707 | 52.38 | 0.64 |
| HT-29 | 38.37 | 4.91 |
| LS147T | 13.62 | 3.87 |
| Pancreatic (3/10) | | |
| **SW 1990 | 78.15 | 1.21 |
| *Panc 2.03 | 22.28 | 4.37 |
| *Panc 4.14 | 21.82 | 2.60 |
| Panc 9.6.94 | 27.28 | 8.47 |
| Panc-1 | 7.82 | 3.69 |
| Panc 3.27 | 6.98 | 5.44 |
| ASPC-1 | 3.09 | 2.36 |
| CAPAN-1 | −1.34 | 2.27 |
| Panc 2.5 | −1.79 | 6.08 |
| MIA PaCa-2 | −4.38 | 1.94 |
| Epidermoid (0/1) | | |
| A431 | −31.12 | 8.55 |

*Tumor cell line generating MDSC with statistically significant mean suppression of autologous T cells ($p < 0.05$)
**Tumor cell line generating MDSC with strong suppression of T cells (mean suppression ≥ 50%)

Table 1 shows that forty-five of 100 human solid tumor cell lines induce functionally suppressive $CD33^+$ myeloid suppressor cells from volunteer normal human PBMC after one-week co-culture in vitro. Shown in table 1 are results for Control, HNSCC, Thyroid, Brain, Melanoma, Cervical/Endometrial, Ovarian, Breast, and Bladder cell types, Sarcomas, Lung Non-small cell, Small Cell, Mesothelioma, Liver, Renal, Prostate, Gastric, Colorectal, Pancreatic, and Epidermoid cell types. Tumor cell lines inducing $CD33^+$ with statistically significant suppressive function are indicated with the symbol "*", and those with strong MDSC inducing capacity (mean T cell suppression by $CD33^+$ cells≥50%) are indicated by "**". $CD33^+$ cells from PBMC cultured in complete medium alone (non-suppressive control) and cytokine-induced MDSC (GM-CSF+IL-6, suppressive control) were run in parallel for comparison.

MDSC-Induction Capacity Correlates with Tumor Cell Line Expression of IL-16, IL-6, TNFα, VEGF, and GM-CSF To elucidate the potential mechanisms underlying the observed differences in myeloid suppressor cell induction by tumor cell lines, the expression of previously reported MDSC-inducing immune modulatory factors (c-kitL, COX2, FLT3L, GM-CSF, IL-1β, IL-4, IL-6, IL-10, IDO, iNOS, M-CSF, TGFβ, TNFα, VEGF) was examined for a group of eight HNSCC cell lines using quantitative RT-PCR techniques (18,24,26). $CD33^+$ MDSC-induction capacity correlated directly with tumor cell line expression of IL-1β, IL-6, TNFα, VEGF, and GM-CSF (Table 2). Differential gene expression of IL-6, TNFα, VEGF, and GM-CSF was confirmed at the protein level by ELISA techniques (FIG. 2A-D), but IL-1β levels were below the sensitivity of the assay.

TABLE 2

| | Average % Suppression by induced MDSC | | Tumor-derived factors | | | | |
|---|---|---|---|---|---|---|---|
| | | | IL-1β | IL-6 | THFα | VEGF | GM-CSF |
| MDSC-Induction Capacity | 92 | SCCL-MT1 | 362.791 | 10.963 | 0.639 | 0.355 | 0.018 |
| | 88 | USC-HN2 | 295.583 | 7.818 | 4.040 | 0.798 | 0.506 |
| | 66 | SCC-4 | 136.442 | 4.887 | 4.263 | 0.100 | 0.063 |
| | 66 | CAL-27 | 100.526 | 10.257 | 3.104 | 0.536 | 0.014 |
| | 59 | SW 451 | 1.935 | 4.253 | 0.979 | 0.780 | 0.295 |
| | 31 | FaDu | 38.225 | 0.535 | 0.036 | 0.190 | 0.002 |
| | 17 | RPMI 2650 | 0.165 | 0.017 | 0.104 | 0.148 | 0.010 |
| | −13 | SW 2224 | 0.009 | 3.442 | 0.208 | 0.088 | 0.026 |
| | | p-value | 0.0001 | 0.0032 | 0.0138 | 0.0008 | 0.0472 |

Expression of ten putative MDSC-inducing factors was measured in MDSC-inducing and non-inducing head and neck squamous cell carcinoma (HNSCC) cell lines by qRT-PCR. As shown in Table 2, increased MDSC-induction capacity was associated with greater expression of IL-1β, IL-6, TNFα, and VEGF (p<0.05). [Mean fold change (n=2) relative to reference RNA (gray=increased=fold change>1, white=decreased expression=fold change<1).]

Figure 3:
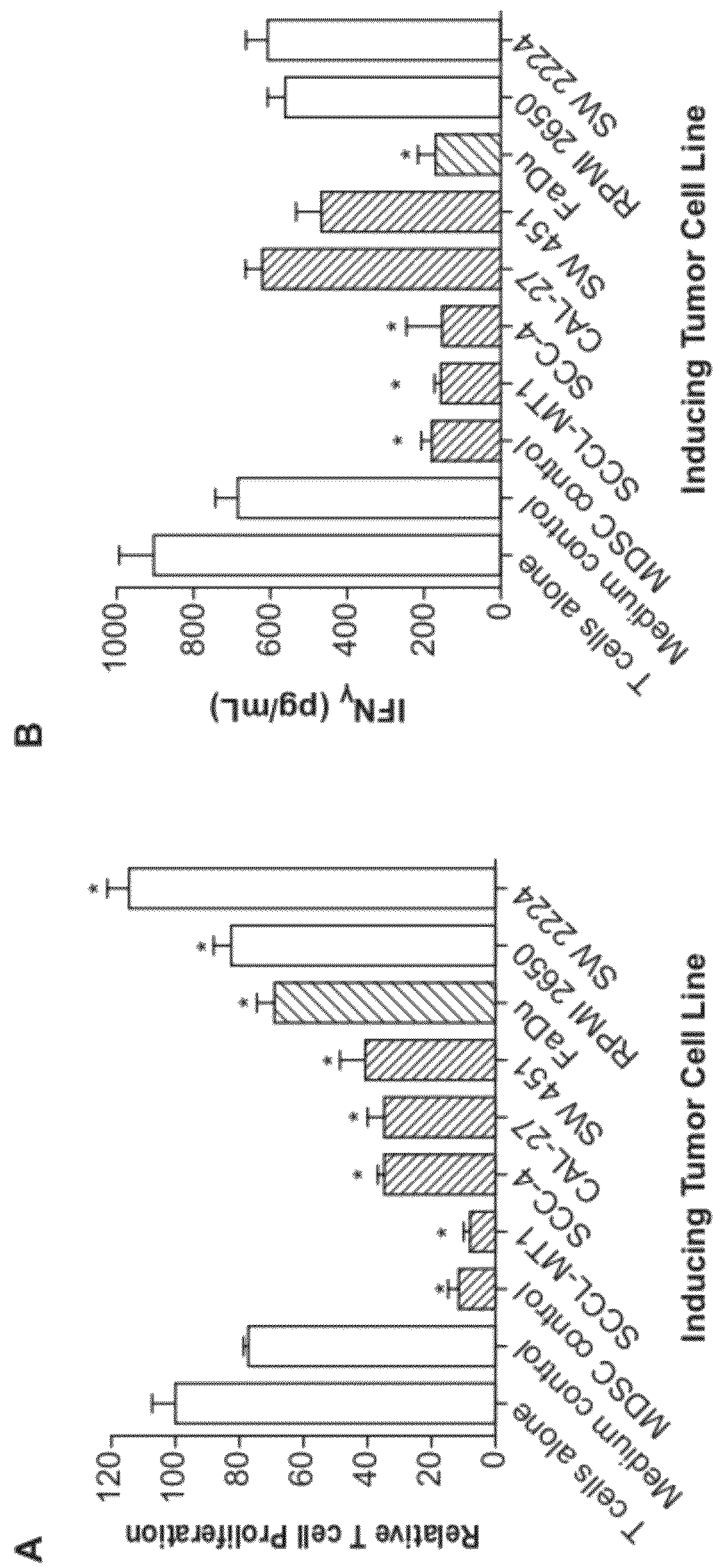
FIG. 3. HNSCC-induced MDSC inhibit autologous T cell proliferation and IFNγ production. A subset of HNSCC cell lines induces a CD33$^+$ population with suppressive function characteristic of MDSC, including inhibition of autologous CD8$^+$ T cell proliferation (A) and IFNγ secretion (B). Tumor cell lines are grouped by strength of MDSC induction: strong (black), weak (gray), and non-inducing (white). For both graphs, mean shown (n≥2 donors)±SEM. * indicates statistical significance, $p<0.05$.

Suppressive CD33+ Myeloid Cells Inhibit Both CD8+ T Cell Proliferation and IFNγ Production To characterize further CD33+ suppressor cells generated by tumor cell line co-culture, IFNγ production was evaluated in addition to T cell proliferation in MDSC suppression assays from co-culture with seven different HNSCC cell lines: CAL-27, FaDu, RPMI 2650, SCC-4, SCCL-MT1, SW 2224, and SW 451 (FIGS. 3A and 3B). The suppressive capability of HNSCC induced CD33+ MDSC was compared with that of a positive T cell proliferation control (T cells alone), an induction negative control of CD33+ cells isolated from PBMC cultured in medium only, and an induction positive control of CD33+ cells isolated from PBMC cultured with GM-CSF and IL-6. In comparison with T cells alone, CD33+ cells induced by SCCL-MT1, SCC-4, CAL-27, SW 451 and the induction positive control demonstrated statistically significant strong inhibition of autologous T cell proliferation, while FaDu induced weakly suppressive MDSC (p<0.05). Consistent with strong suppression, CD33+ cells induced by SCCL-MT1, SCC-4, and the induction positive control significantly inhibited IFNγ production (p<0.05). Although CD33+ suppressor cells induced by FaDu did not strongly inhibit T cell proliferation, these co-cultures did demonstrate significantly decreased IFNα production (p<0.05). Conversely, Cal-27 and SW 451 induced MDSC that strongly suppressed T cell proliferation, but only weakly inhibited IFNγ. CD33+ cells induced by RPMI 2650 and SW 2224 did not demonstrate suppression of T cell proliferation or inhibition of IFNγ. These findings suggest that MDSC may impede T cell responses through multiple avenues, including inhibition of proliferation and IFNγ production.

Preferential Induction of CD11b+ MDSC by Human Cancer Cell Lines

Figure 4:
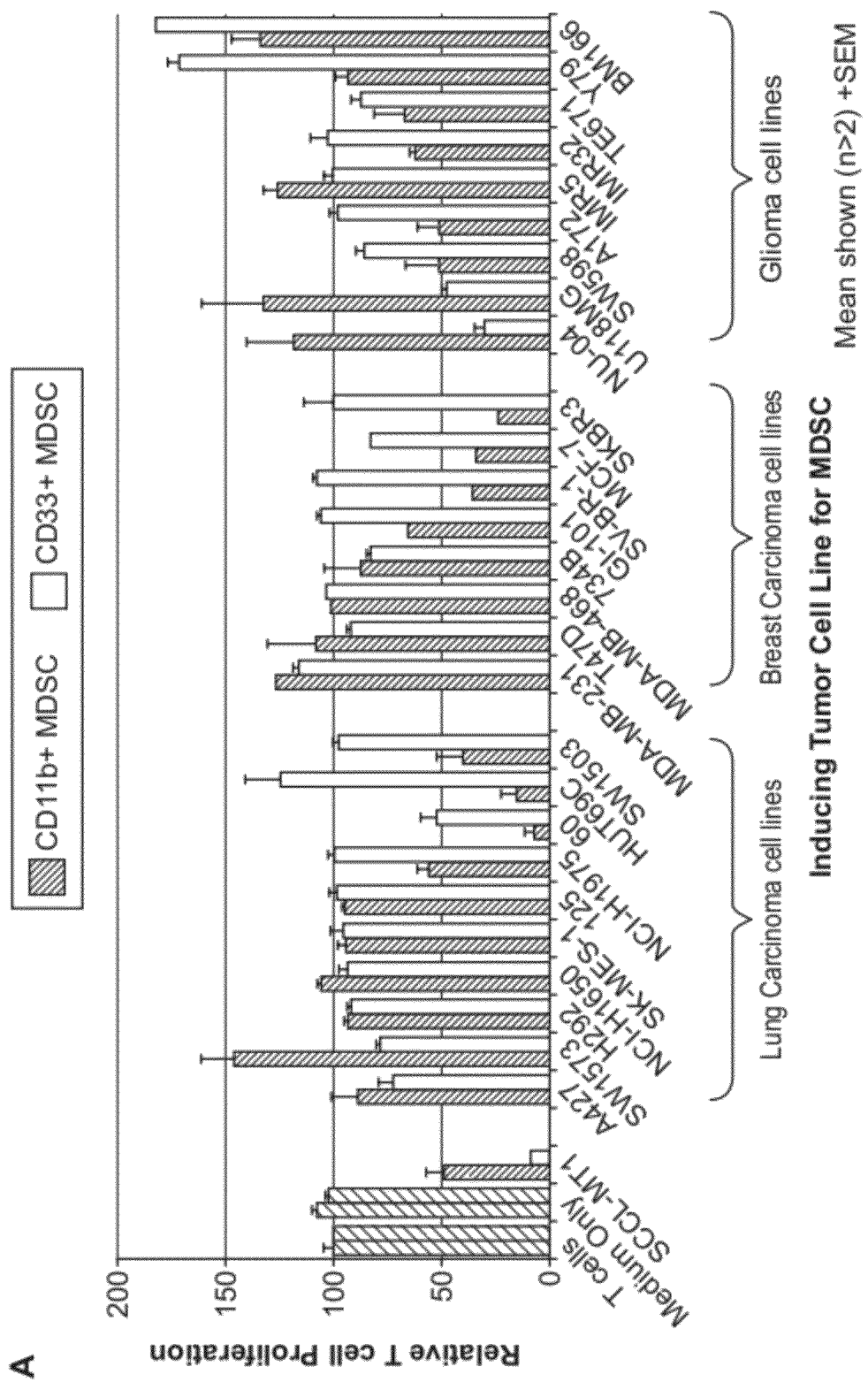
FIG. 4. Human breast carcinoma, lung carcinoma, and glioma cell lines preferentially induce CD11b$^+$ MDSC over CD33$^+$ MDSC and identify CD11b$^+$ MDSC as a second subset. A. CD11b$^+$ cells from breast cancer, lung cancer, or glioma cell line-PBMC co-cultures were evaluated for suppressive function against CD3/CD28 stimulated autologous T cells. Mean (n=2) T cell proliferation±SEM or T cell proliferation (n=1) is shown from Suppression Assays of CD33$^+$ or CD11b$^+$ cells with autologous T cells, respectively. B. CD11b$^+$ MDSC subset can be induced from normal donor PBMC by cytokines FLT3L and TGFβ. Mean shown (n=3) ±SEM. * indicates statistically significant in mean T cell proliferation compared with T cells alone ($p<0.05$).
Figure 4:
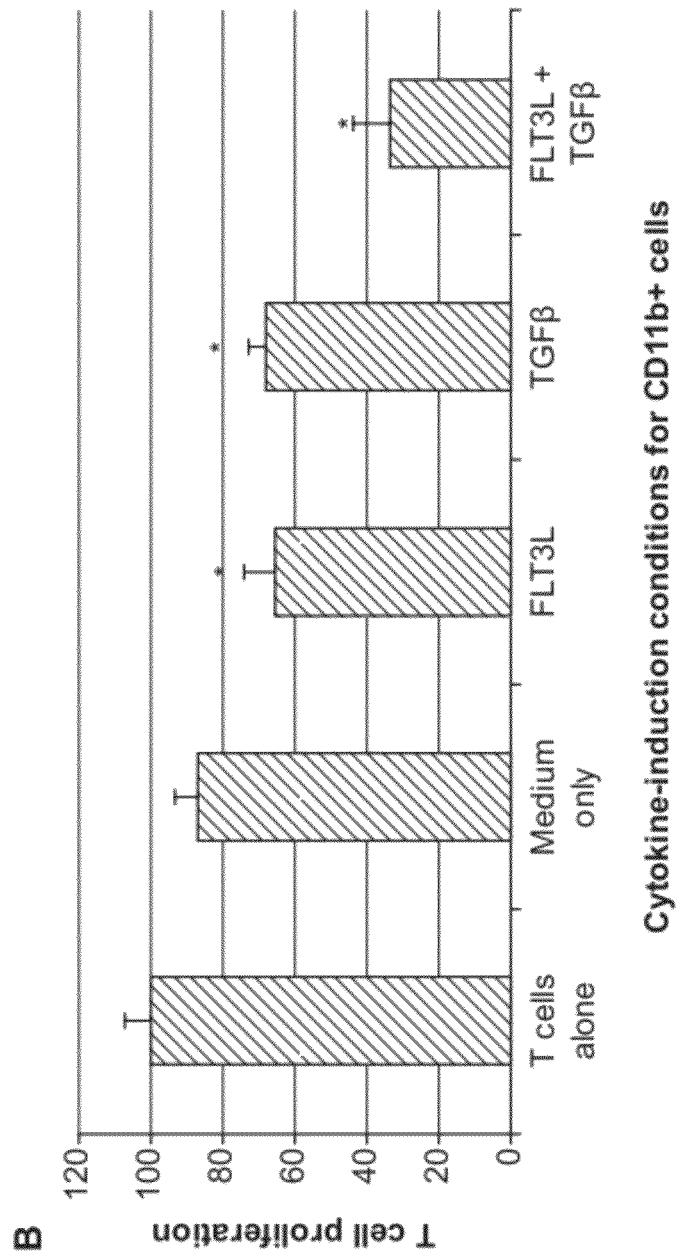

To clarify the apparent absence of CD33+ MDSC induction by breast carcinoma cell lines, CD11b+ cells from breast cancer cell line-PBMC co-cultures were evaluated for suppressive function against CD3/CD28 stimulated autologous T cells (FIG. 4). In these studies, 4/8 human breast cancer cell lines induced CD11b+ suppressor cells. Mean (n=2) T cell proliferation or T cell proliferation (n=1) is shown from suppression assays of CD33+ or CD11b+ cells with autologous T cells, respectively (FIG. 4). Consequently, breast carcinoma cell lines preferentially induced CD11b+ MDSC, even though no human breast cancer cell lines (0/9) tested generated suppressive CD33+ cells, suggesting that this component of the MAC-1 phagocytic complex may be a more specific marker for the subset of MDSC induced by breast cancer tumor cells. Non-small cell lung carcinoma cell lines and glioma cell lines, which had a low frequency of CD33+ MDSC induction (3/10 and 2/9, respectively), were found also to induce with moderate frequency this CD11b+ MDSC subset (4/10 and 4/9, respectively). (FIG. 4). These experiments identify a second subset of human MDSC arising in the cancer setting. Taken collectively with the survey of CD33+ MDSC induction, these data indicate that the induction of MDSC is a universal feature of human cancers with some variation in the phenotype of induced MDSC subsets observed.

Morphology of Human CD33+ and CD11b+ Suppressor Cells Induced by Tumor Cell Lines Two subsets of human myeloid cells (CD11b+ or CD33+ cells) induced from normal donor PBMC by tumor-cell line co-culture have suppressive capacity. The morphology of suppressive tumor-co-cultured CD33+ and CD11b+ populations was compared to that of freshly isolated PBMC and myeloid cells cultured in medium only by Wright-Giemsa staining. Healthy donor PBMC showed occasional mononuclear cells with pale and scant cytoplasm, scattered amongst predominant lymphocytes. CD33+ cells from PBMC cultured in medium alone (with rhGM-CSF for growth support) for one week were predominantly large, mononuclear cells having abundant basophilic cytoplasm with occasional granulocytes and other myeloid lineage cells (e.g. eosinophils). In contrast to the mature lineages seen in medium only myeloid cells, CD33+ and CD11b+ suppressor cells isolated from PBMC after tumor co-culture showed an abundance of immature cells, including metamyelocytes or band cells and blast-like cells. No obvious morphologic differences were observed between CD33+ and CD11b+ MDSC.

Figure 5:
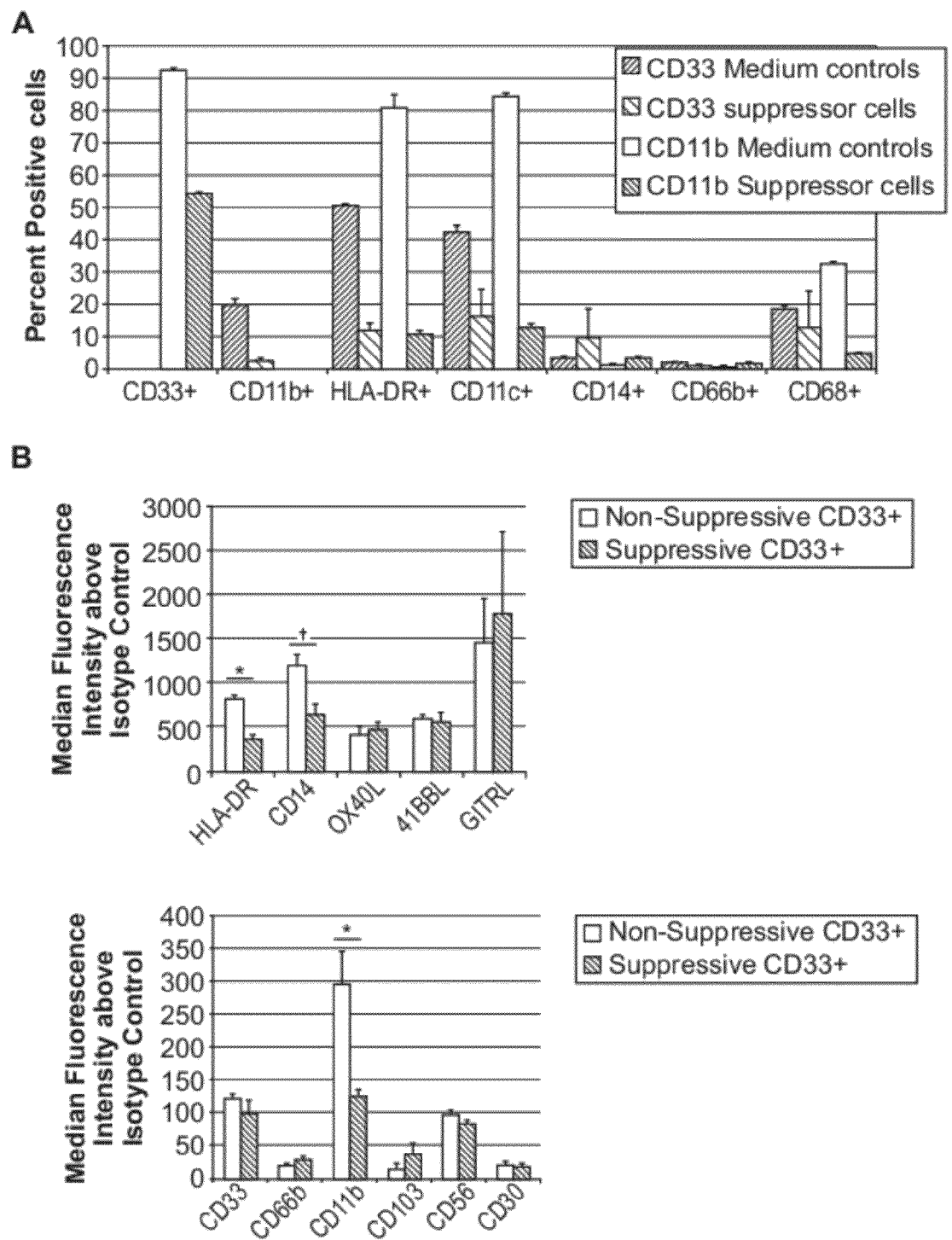
FIG. 5. Characterization of CD33$^+$ and CD11b$^+$ tumor cell line-induced MDSC. A. Phenotype of HNSCC cell line-induced CD33$^+$ and breast cancer cell line-induced CD11b$^+$ MDSC compared with medium only, non-suppressive CD33$^+$ and CD11b$^+$ cells as measured by flow cytometry. Mean percent positive cells (n≥2)±SD shown. B. Expression of antigen presenting cell (left) and suppressor cell (right) markers on strongly suppressive (induced by HNSCC cell lines SCCL-MT1, SCC-4, CAL-27) versus non-suppressive (induced by SW 2224, RPMI 2650, or medium only) CD33$^+$ myeloid cells as measured by flow cytometry. Mean fluorescence above isotype control (data from 3 unique donors; mean shown for all three induction conditions (n=9)±SEM). For comparison of mean values between suppressive cell and non-suppressive cells * indicates statistical significance, $p<0.05$ and t indicates $p=0.59$.

Phenotype of MDSC Shows CD33+ and CD11b+ subsets, both HLA-DR$^{low}$ and Lineage$^-$ Further characterization of CD33+ and CD11b+ MDSC subsets examined their expression of a wide range of proposed MDSC and mature innate immune cell markers (CD33, CD11b, CD66b, CD14, CD11c, HLA-DR, GITRL, OX40L, 41BBL (CD137L), CD56). Human MDSC were isolated by magnetic bead column separation after one-week co-culture with SCCL-MT1 or USC-HN2 HNSCC cell lines (CD33+) or MCF-7 breast cancer cell line (CD11b+) and non-suppressive CD33+ or CD11b+ control cells were isolated from medium only PBMC cultures. The purity for column isolated populations was found to be >90% by flow cytometry. Positivity for MDSC and mature myeloid lineage markers was measured by flow cytometry for each population and compared between CD33+ and CD11b+ MDSC subsets and between suppressive and non-suppressive populations (FIG. 5). CD11b expression levels were inversely correlated with suppressive function in CD33+ cells in these studies, and similarly CD33 positivity was inversely correlated with suppressive function in CD11b+ cells, suggesting a divergence in the two populations during induction (FIG. 5A). Both CD33+ and CD11b+ suppressive populations showed decreased expression of activation marker HLA-DR and mature DC marker CD11c compared with non-suppressive populations of CD11b+ and CD33+ cells. These data are consistent with an accumulation of immature myeloid lineage cells coincident with the induction of suppressive function in either CD11b+ or CD33+ cells. Differentiated DC markers and T cell co-stimulatory ligands were further examined on the CD33+ subset of MDSC and found to be expressed at similarly low levels between suppressive and non-suppressive CD33+ cells isolated from tumor co-cultures (p=NS) (FIG. 5B), suggesting that the maturation and antigen presenting defects of MDSC are not primary in T cell suppression. Macrophage marker CD68 and granulocyte marker CD66b expression were low or absent and not differentially expressed by suppressive and non-suppressive CD33+ or CD11b+ cells in this study.

Tumor-Induced Myeloid Suppressor Cells Over-Express iNOS, TGFβ, NOX2, VEGF, and ARG-1

Figure 6:
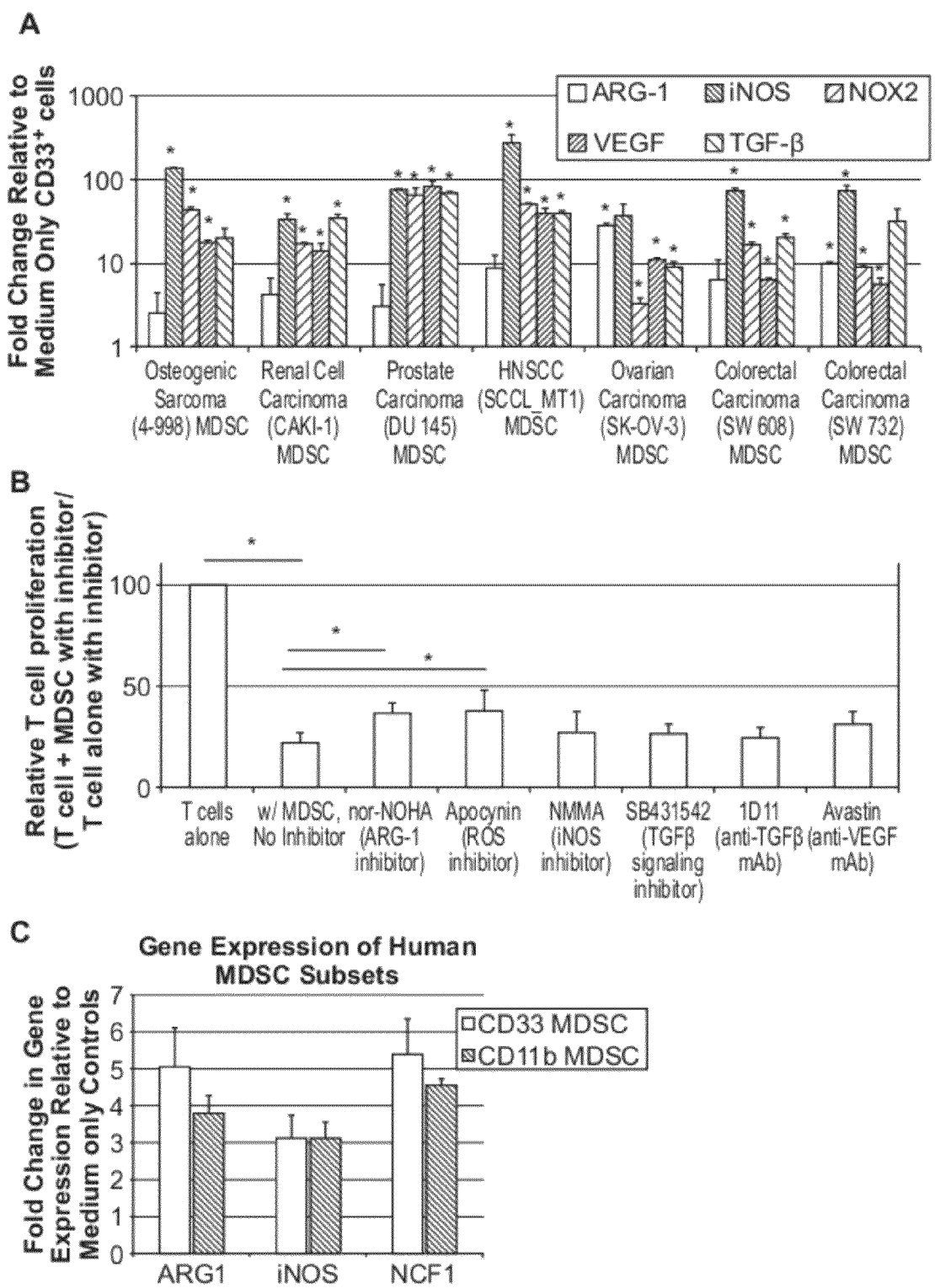
FIG. 6. Human MDSC mediate suppression through up-regulation of ARG-1, NOX2, iNOS, VEGF, and TGFβ. A. Expression of putative suppressive genes ARG-1, iNOS, NOX2-component NCF1, VEGF, and TGFβ in a subset of tumor cell line-induced CD33$^+$ MDSC. * indicates statistical significance, $p<0.05$, by ANOVA followed by Dunnett test for pairwise comparisons to medium only CD33$^+$ controls for expression measured for each gene. B. Tumor cell line-induced CD33$^+$ MDSC inhibit proliferation of autologous, CD3/CD28-stimulated T cells. Specific inhibitors of MDSC suppressive mechanisms ARG-1 and NOX2 mediate partial but incomplete reversal of suppression. * indicates statistical significant difference in mean T cell proliferation (mean shown+SEM, n≥7 for each inhibitor, data from 2 independent experiments with similar results), $p<0.05$, by ANOVA followed by Tukey test for pairwise comparisons. C. Comparison of ARG-1, iNOS, and NOX2-component NCF1 gene expression in CD33$^+$ and CD11b$^+$ human MDSC revealed similar levels of expression between these subsets. Mean fold change shown relative to medium only controls (n=3 unique donors for MDSC from co-cultures with each of three inducing tumor models)±SEM. No statistically significant difference between mean expression between subsets as determined by Student's t test for each gene observed.

Further characterization of tumor-induced canonical CD33+ MDSC subset by analysis of the expression of putative MDSC suppression genes was performed. For these studies, expression of putative suppression genes was measured in tumor cell line-induced MDSC, including those induced by SCCL-MT1 HNSCC cell line and those induced by 4-998 osteogenic sarcoma, DU 145 prostate carcinoma, CAKI-1 renal cell carcinoma, SK-OV-3 ovarian carcinoma, and SW 608 and SW 732 colorectal adenocarcinoma cell lines (FIG. 6A), and compared to expression levels in normal, non-suppressive CD33$^+$ myeloid cells from medium only cultures. These MDSC consistently showed statistically significant up-regulation of arginase (ARG-1), inducible nitric oxide synthase (iNOS), NADPH oxidase (NOX2), vascular endothelial growth factor (VEGF), and/or transforming growth factor (TGF)β compared with control CD33$^+$ cells from medium-only cultures (FIG. 6A). Subtle variations were observed in the gene expression patterns of these tumor-induced MDSC. To determine the dominant mechanism of T cell suppression by this canonical CD33$^+$ MDSC subset, suppression assays were repeated in the presence or absence of specific inhibitors of ARG-1 (nor-NOHA), iNOS (L-NMMA), NOX2 (apocynin), VEGF (neutralizing antibody Avastin), or TGFβ1 (SB431542 or neutralizing antibody 1D11). In these studies no one inhibitor was found to completely reverse suppression (FIG. 6B), consistent with the pleotropic actions of monocytic MDSC, but inhibitors of ARG-1 and NOX2 did produce statistically significant decreases in suppression by CD33$^+$ MDSC. These results were confirmed by siRNA knockdown of individual suppression genes: ARG-1, iNOS, NCF1 (NOX2 component), TGFβ1, or VEGFA. A comparison of ARG-1, iNOS, and NOX2-component NCF1 gene expression in CD33$^+$ and CD11b$^+$ human MDSC induced by HNSCC or breast carcinoma cell lines revealed similar levels of expression between these subsets with a trend toward increased ARG-1 and NOX2 expression in CD33$^+$ MDSC (FIG. 6C).

Figure 7:
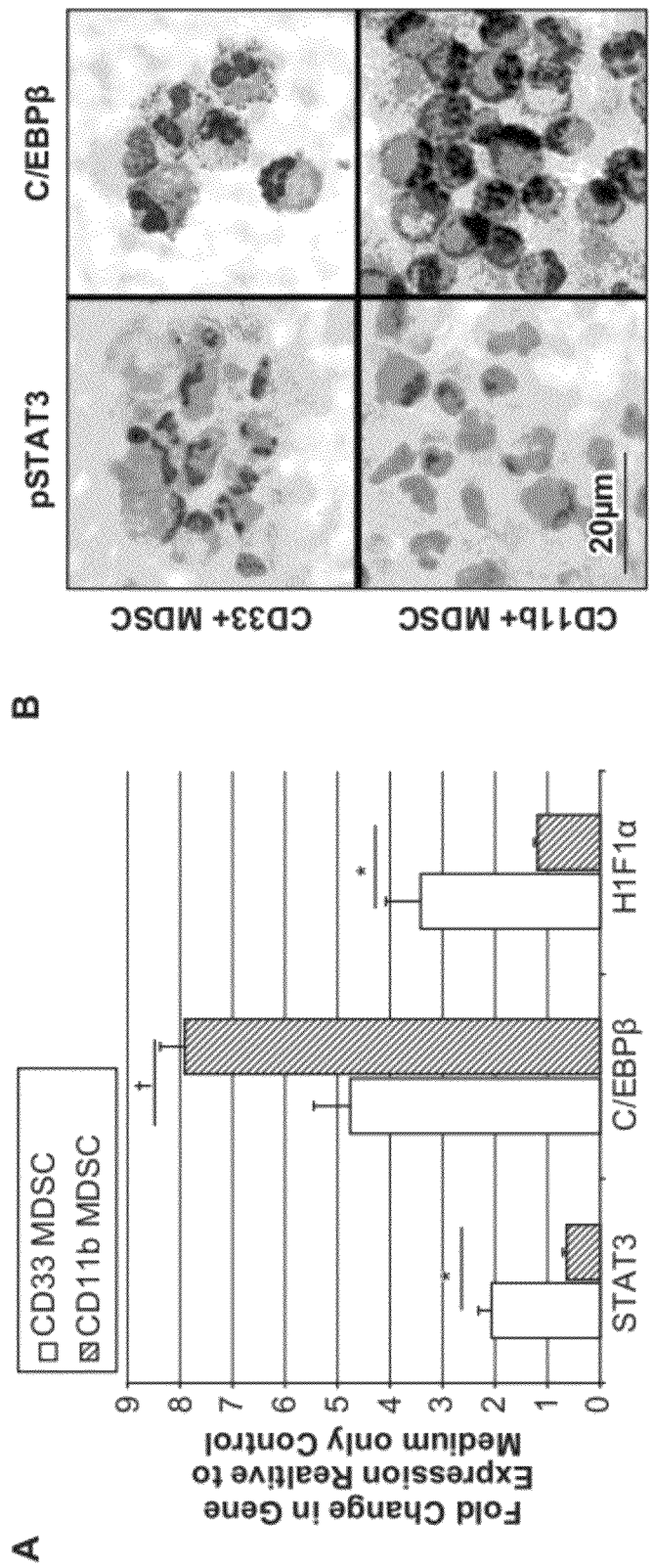
FIG. 7. Transcription factors promoting human MDSC suppressive function. A. HIF1α and STAT3 expression in tumor cell line-induced CD33$^+$ or CD11b$^+$ MDSC compared with medium only controls as measured by qRT-PCR. Mean shown (data from six unique donors, two independent experiments)±SEM; * indicates statistical significance, $p<0.05$, † indicates $p=0.06$ for pairwise comparisons of CD33$^+$ versus CD11b$^+$ MDSC. B. Immunohistochemisty of p-STAT3 and C/EBPβ in CD33$^+$ (top panels) and CD11b$^+$ (bottom panels) MDSC. Representative images shown from multiple samples stained (200×original magnification). C. Activation of human MDSC subsets by toll-like receptor agonist lipopolysaccharide produces up-regulation of HIF1α, C/EBPβ, and STAT3, concurrent with increased expression of suppressive mediators ARG-1, iNOS, and NOX2. Mean shown (data from three unique donors)±SEM. D. Transcriptional changes in MDSC subsets associated with inactivation of suppressive function. Reversal of CD33$^+$ MDSC suppressive function by ATRA, sunitinib, and CXB correlated with decreased STAT3 and HIF1α expression (arrows). Functional inhibition of human CD11b$^+$ MDSC by ATRA and Sunitinib correlated with decreased C/EBPβ levels (arrow), but no change in STAT3 and HIF1α mRNA levels. CXB was not found to have inhibitory actions on CD11b$^+$ MDSC and it was not observed to decrease C/EBPβ levels in this population. Mean shown (data from three unique donors)±SEM, * indicates statistically significant decrease ($p<0.05$) in transcript level in drug-treated MDSC compared with untreated MDSC (ANOVA with Dunnett post-test).
Figure 7:
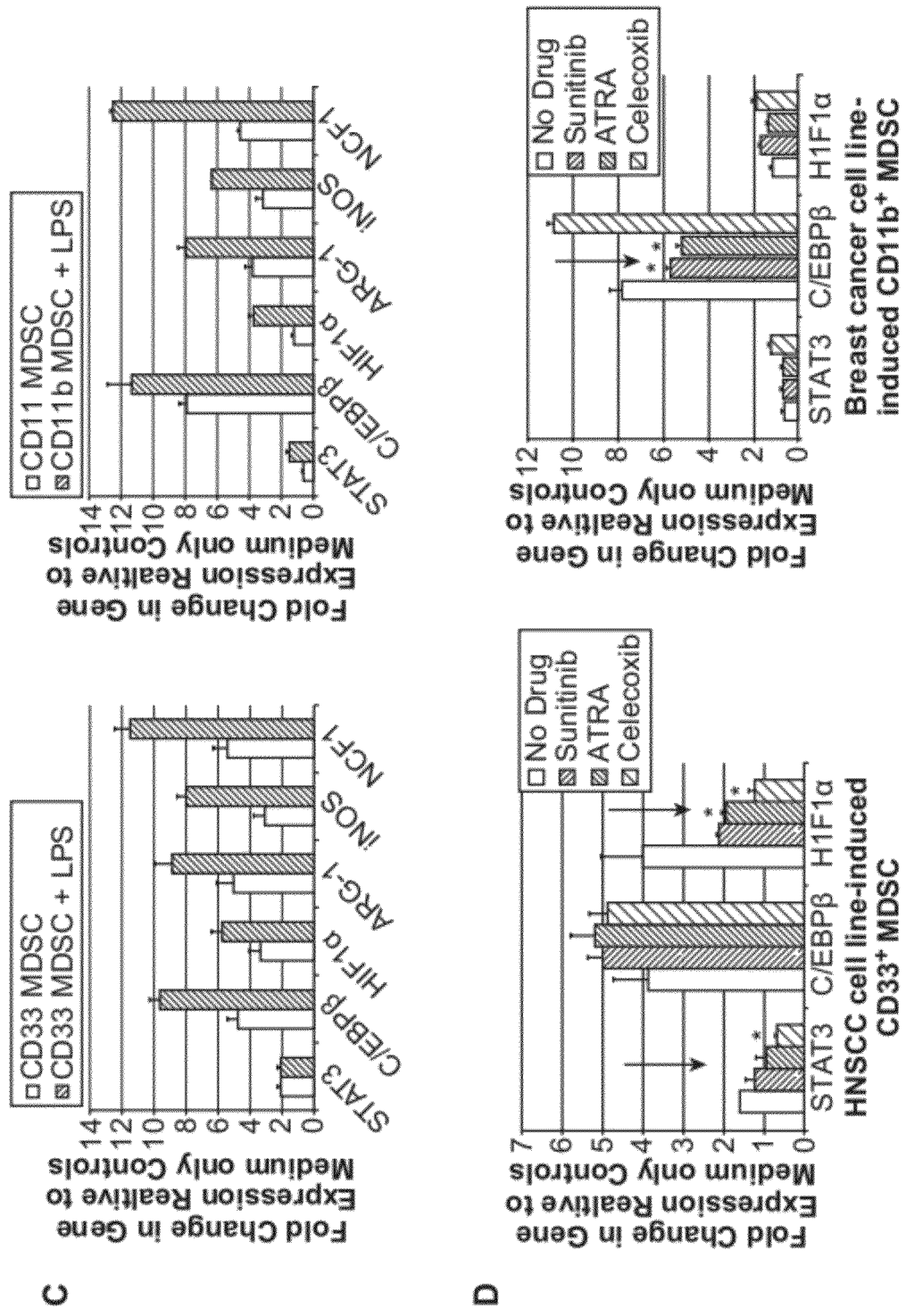
Figure 11A:
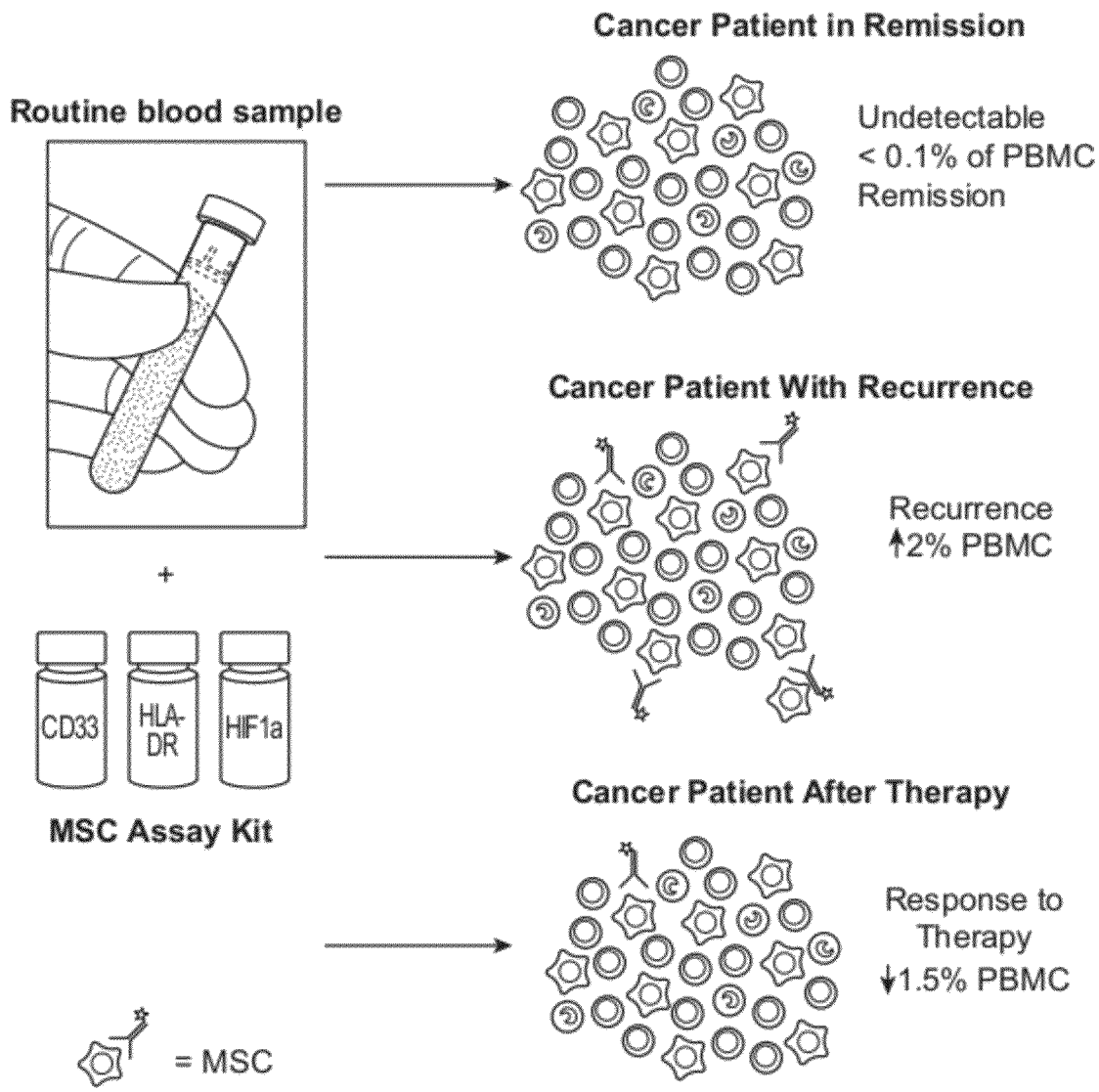
FIG. 11. Clinical assay for cancer detection and monitoring. A. Schematic showing an embodiment of a minimally-invasive clinical assay for cancer detection and monitoring. Patient peripheral blood cells are analyzed by flow cytometry for the presence of myeloid suppressor cells (MDSC) as a marker for tumor presence. Active MDSC are distinguished from normal blood cells by a 3-marker phenotype that correlates directly with suppressive function. Accumulation of active MDSC correlates directly with disease stage and tumor burden, allowing tracking of disease stage, tumor response to therapy, and tumor recurrence or progression by a simple blood test. B and C. Demonstration of MDSC in the peripheral blood of cancer patients having the phenotype: $CD33^+$ $HLA-DR^{low}HIF1\alpha^+$. Twenty milliliters of peripheral blood was collected from normal, healthy volunteers (B) or HNSCC cancer patients (C) and PBMC were isolated by density gradient separation. PBMC were stained for $CD33^+$ and $HLA-DR^+$ using fluorescence-labeled monoclonal antibodies, then cells were fixed and permeabilized for intracellular staining of HIF1α by a third antibody. Stained sample PBMC and isotype controls were analyzed on a FACSCalibur flow cytometer using CellQuestPro software and collecting at least 50,000 live leukocyte events (gated as shown in the middle panels). $HLA-DR^{low}HIF1\alpha^+$ cells were found to be 0.12-1.99% of myeloid cells in normal donor controls (n=3) compared with 16.23-15.78% of myeloid cells in head and neck cancer patients (n=2); representative dot plots are shown. The following tabulated data depicts the results from the FACS analysis in FIG. 11.
Figure 11B:
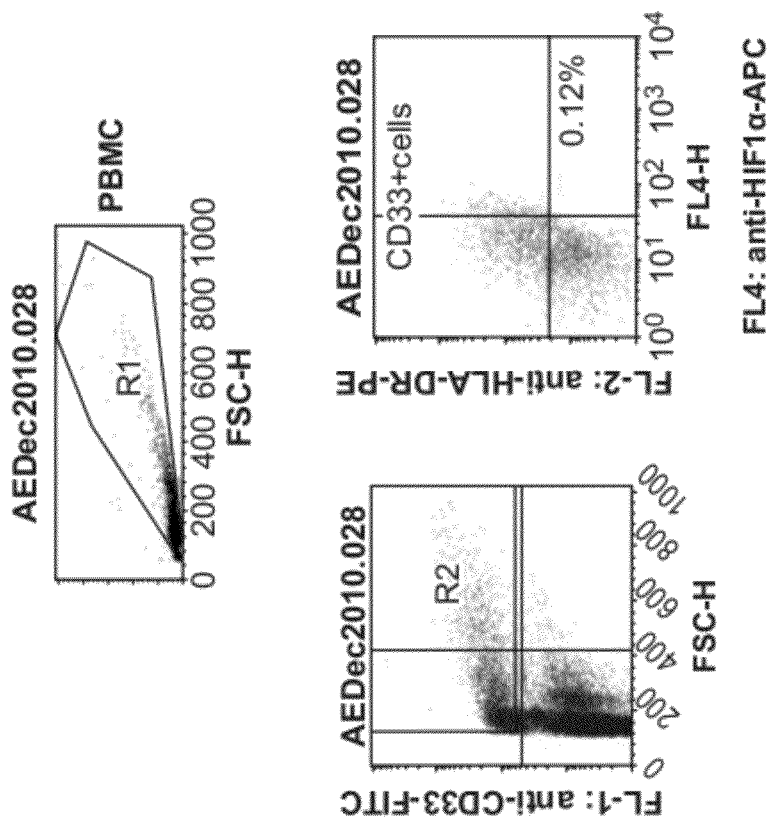
Figure 11C:
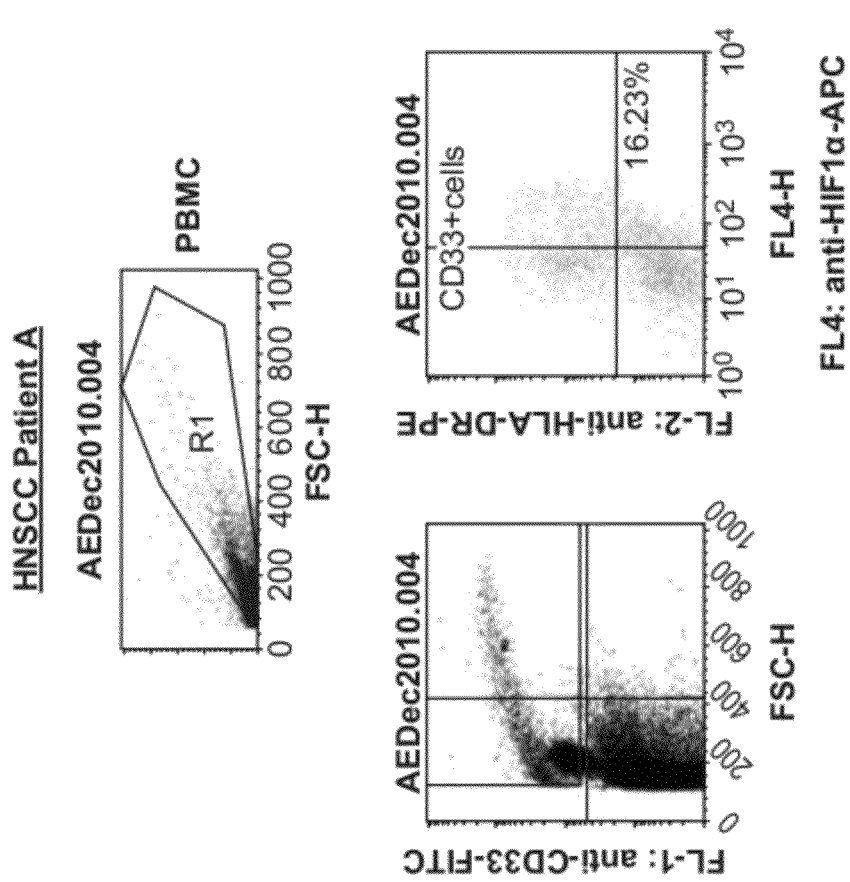
Figure 11C:
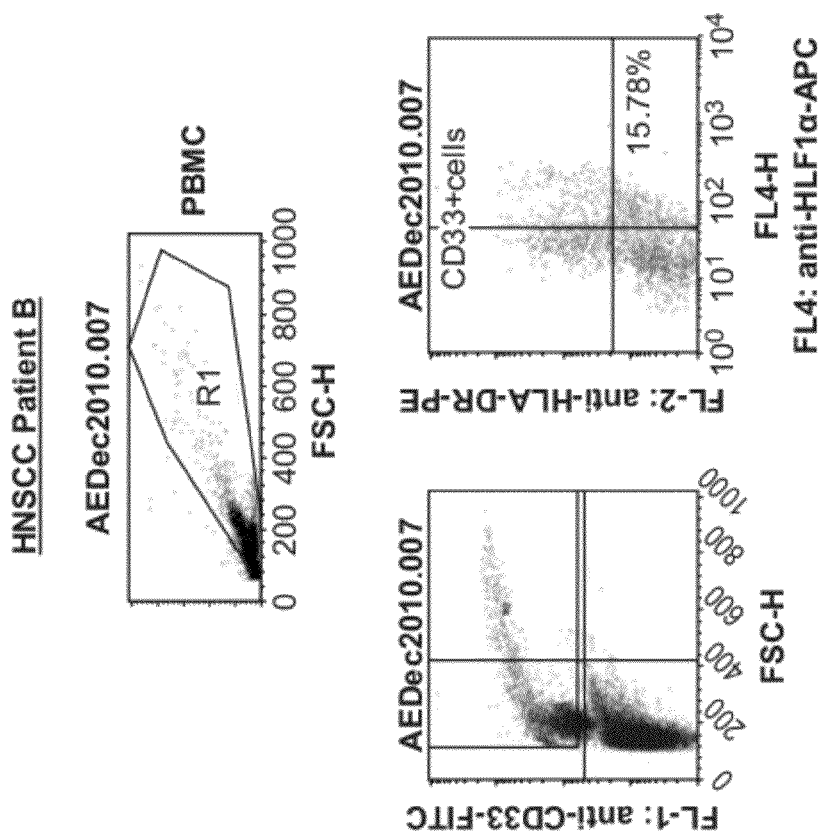

Higher Hif1α, STAT3, and C/EBPβ Gene Expression Distinguish Tumor Cell Line-Induced Human MDSC from Normal Myeloid Cells We examined the expression of HIF1α, STAT3, and C/EBPβ in tumor cell line, (SCCL-MT1 or USC-HN2)-induced CD33$^+$ or (MCF7 breast carcinoma) CD11b$^+$ human suppressor cells compared to medium only controls by qRT-PCR (data from six unique donors, two independent experiments) (FIG. 7A) and immunohistochemistry (FIG. 7B). CD33$^+$ MDSC showed stronger up-regulation of STAT3 and HIF1α while CD11b$^+$ MDSC showed comparably greater up-regulation of C/EBPβ (FIG. 7A). Treatment of either CD33$^+$ or CD11b$^+$ tumor-cell line-induced MDSC with lipopolysaccharide (LPS), a known activator of MDSC function, caused further up-regulation of STAT3, C/EBPβ, and HIF1α concurrent with increased expression of ARG-1, iNOS, and NOX2-component NCF1 (FIG. 7C).

Gene expression patterns in ATRA, Sunitinb, or CXB-treated CD33$^+$ or CD11b$^+$ human MDSC were determined (FIG. 7D). Inhibition of human CD33$^+$ MDSC by ATRA, Sunitinib, and Celecoxib correlated with decreased STAT3 and HIF1α transcription. In comparison, inhibition of human CD11b$^+$ MDSC by ATRA and Sunitinib correlated with decreased C/EBPβ levels, but no change in STAT3 and HIF1α mRNA levels. Celecoxib was not found to have inhibitory actions on CD11b$^+$ MDSC and it was not observed to decrease C/EBPβ levels in this population. These data suggest that HIF1α, STAT3, and C/EBPβ are key transcription factors related to suppressive function in tumor cell line-induced human MDSC.

It should be understood that although the present disclosure has been specifically disclosed by preferred embodiments and optional features, modification, improvement and variation of the disclosure embodied therein herein disclosed may be resorted to by those skilled in the art, and that such modifications, improvements and variations are considered to be within the scope of this disclosure. The materials, methods, and examples provided here are representative of preferred embodiments, are exemplary, and are not intended as limitations on the scope of the disclosure.

The disclosure has been described broadly and generically herein. Each of the narrower species and subgeneric groupings falling within the generic disclosure also form part of the disclosure. This includes the generic description of the disclosure with a proviso or negative limitation removing any subject matter from the genus, regardless of whether or not the excised material is specifically recited herein.

In addition, where features or aspects of the disclosure are described in terms of Markush groups, those skilled in the art will recognize that the disclosure is also thereby described in terms of any individual member or subgroup of members of the Markush group.

All publications, patent applications, patents, and other references mentioned herein are expressly incorporated by reference in their entirety, to the same extent as if each were incorporated by reference individually. In case of conflict, the present specification, including definitions, will control.

REFERENCES

1. Stewart, T. J., and S. I. Abrams. 2008. How tumours escape mass destruction. *Oncogene.* 27: 5894-5903.
2. Bak, S. P., A. Alonso, M. J. Turk, and B. Berwin. 2008. Murine ovarian cancer vascular leukocytes require arginase-1 activity for T cell suppression. *Mol Immunol.* 46: 258-268.
3. Nagaraj, S., and D. I. Gabrilovich. 2008. Tumor escape mechanism governed by myeloid-derived suppressor cells. *Cancer Res.* 68: 2561-2563.
4. Corzo, C. A., M. J. Cotter, P. Cheng, F. Cheng, S. Kusmartsev, E. Sotomayor, T. Padhya, T. V. McCaffrey, J. C. McCaffrey, and D. I. Gabrilovich. 2009. Mechanism regulating reactive oxygen species in tumor-induced myeloid-derived suppressor cells. *J Immunol.* 182: 5693-5701.
5. Donkor, M. K., E. Lahue, T. A. f Ioke, L. R. Shafer, U. Coskun, J. C. Solheim, D. Gulen, J. Bishay, and J. E. Talmadge. 2009. Mammary tumor heterogeneity in the expansion of myeloid-derived suppressor cells. *Int Immunopharmacol.* 9: 937-948.
6. Srivastava, M. K., P. Sinha, V. K. Clements, P. Rodriguez, S. Ostrand-Rosenberg. 2010. Myeloid-derived suppressor cells inhibit T-cell activation by depleting cystine and cysteine. *Cancer Res.* 70: 68-77.
7. Serafini, P., S. Mgebroff, K. Noonan, and I. Borrello. 2008. Myeloid-derived suppressor cells promote cross-tolerance in B cell lymphoma by expanding regulatory T cells. *Cancer Res.* 68: 5439-5449.
8. Dumitriu, I. E., D. R. Dunbar, S. E. Howie, T. Sethi, and C. D. Gregory. 2009. Human dendritic cells produce TGF-beta 1 under the influence of lung carcinoma cells and prime the differentiation of CD4+CD25+Foxp3+ regulatory T cells. *J Immunol.* 182: 2795-2807.
9. Gabrilovich, D. I., and S. Nagaraj. 2009. Myeloid-derived suppressor cells as regulators of the immune system. *Nat Rev Immunol.* 9: 162-174.
10. Hellwig-Bürgel, T., D. P. Stiehl, A. E. Wagner, E. Metzen, and W. Jelkmann. 2005. Review: hypoxia-inducible factor-1 (HIF-1): a novel transcription factor in immune reactions. *J Interferon Cytokine Res.* 25: 297-310.
11. Mandruzzato, S., S. Solito, E. Falisi, S. Francescato, V. Chiarion-Sileni, S. Mocellin, A. Zanon, C. R. Rossi, D. Nitti, V. Bronte, and P. Zanovello. 2009. IL4Ralpha+ myeloid-derived suppressor cell expansion in cancer patients. *J Immunol.* 182: 6562-6568.

12. Hoechst, B., T. Voigtlaender, L. Ormandy, J. Gamrekelashvili, F. Zhao, H. Wedemeyer, F. Lehner, M. P. Manns, T. F. Greten, and F. Korangy. 2009. Myeloid derived suppressor cells inhibit natural killer cells in patients with hepatocellular carcinoma via the NKp30 receptor. Hepatology. 50: 799-807.

13. Liu, C. Y., Y. M. Wang, C. L. Wang, P. H. Feng, H. W. Ko, Y. H. Liu, Y. C. Wu, Y. Chu, F. T. Chung, C. H. Kuo, K. Y. Lee, S. M. Lin, H. C. Lin, C. H. Wang, C. F. Yu, and H. P. Kuo. 2009. Population alterations of L: -arginase- and inducible nitric oxide synthase-expressed CD11b(+)/ CD14(-)/CD15(+)/CD33(+) myeloid-derived suppressor cells and CD8 (+) T lymphocytes in patients with advanced-stage non-small cell lung cancer. *J Cancer Res Clin Oncol.* 136: 35-45.

14. Ko, J. S., A. H. Zea, B. I. Rini, J. L. Ireland, P. Elson, P. Cohen, A. Golshayan, P. A. Rayman, L. Wood, J. Garcia, R. Dreicer, R. Bukowski, and J. H. Finke. 2009. Sunitinib mediates reversal of myeloid-derived suppressor cell accumulation in renal cell carcinoma patients. *Clin Cancer Res.* 15: 2148-2157.

15. Morse, M. A., J. R. Hall, and J. M. Plate. 2009. Countering tumor-induced immunosuppression during immunotherapy for pancreatic cancer. *Expert Opin Biol Ther.* 9: 331-339.

16. Diaz-Montero, C. M., M. L. Salem, M. I. Nishimura, E. Garrett-Mayer, D. J. Cole, and A. J. Montero. 2009. Increased circulating myeloid-derived suppressor cells correlate with clinical cancer stage, metastatic tumor burden, and doxorubicin-cyclophosphamide chemotherapy. *Cancer Immunol Immunother.* 58: 49-59.

17. Peranzoni, E., S. Zilio, I. Marigo, L. Dolcetti, P. Zanovello, S. Mandruzzato, and V. Bronte. 2010. Myeloid-derived suppressor cell heterogeneity and subset definition. *Curr Opin Immunol.* 22: 238-244.

18. Serafini, P., I. Borrello, and V. Bronte. 2006. Myeloid suppressor cells in cancer: recruitment, phenotype, properties, and mechanisms of immune suppression. *Semin Cancer Biol.* 16: 53-65.

19. Zea, A, H., P. C. Rodriguez, M. B. Atkins, C. Hernandez, S. Signoretti, J. Zabaleta, D. McDermott, D. Quiceno, A. Youmans, A. O'Neill, J. Mier, A. C. Ochoa. 2005. Arginase-producing myeloid suppressor cells in renal cell carcinoma patients: a mechanism of tumor evasion. *Cancer Res.* 65: 3044-3048.

20. Filipazzi, P., R. Valenti, V. Huber, L. Pilla, P. Canese, M. Iero, C. Castelli, L. Mariani, G. Parmiani, and L. Rivoltini. 2007. Identification of a new subset of myeloid suppressor cells in peripheral blood of melanoma patients with modulation by a granulocyte-macrophage colony-stimulation factor-based antitumor vaccine. *J Clin Oncol.* 25: 2546-2553.

21. Gordon, I. O., and R. S. Freedman. 2006. Defective antitumor function of monocyte-derived macrophages from epithelial ovarian cancer patients. *Clin Cancer Res.* 12: 1515-1524.

22. Hoechst, B., L. A. Ormandy, M. Ballmaier, F. Lehner, C. Kruger, M. P. Manns, T. F. Greten, and F. Korangy. 2008. A new population of myeloid-derived suppressor cells in hepatocellular carcinoma patients induces CD4(+)CD25 (+)Foxp3(+) T cells. *Gastroenterology.* 135: 234-243.

23. Ostrand-Rosenberg, S., and P. Sinha. 2009. Myeloid-derived suppressor cells: linking inflammation and cancer. *J Immunol.* 182: 4499-4506.

24. Kusmartsev, S., and D. I. Gabrilovich. 2006. Effect of tumor-derived cytokines and growth factors on differentiation and immune suppressive features of myeloid cells in cancer. *Cancer Metastasis Rev.* 25: 323-331.

25. Xiang, X., A. Poliakov, C. Liu, Y. Liu, Z. B. Deng, J. Wang, Z. Cheng, S. V. Shah, G. J. Wang, L. Zhang, W. E. Grizzle, J. Mobley, and H. G. Zhang. 2009. Induction of myeloid-derived suppressor cells by tumor exosomes. *Int J Cancer.* 124: 2621-2633.

26. Lechner, M. G., D. J. Liebertz, and A. L. Epstein. 2010. Characterization of cytokine-induced myeloid-derived suppressor cells from normal human peripheral blood mononuclear cells. *J Immunol.* 185: 2273-2284.

27. Poschke, I., D. Mougiakakos, J. Liansson, G. V. Masucci, and R. Kiessling. 2010. Immature immunosuppressive CD14+HLA-DR−/low cells in melanoma patients are Stat3hi and overexpress CD80, CD83, and DC-sign. *Cancer Res.* 70: 4335-4345.

28. Munera, V., P. J. Popovic, J. Bryk, J. Pribis, D. Caba, B. M. Matta, M. Zenati, and J. B. Ochoa. 2010. Stat 6-dependent induction of myeloid derived suppressor cells after physical injury regulates nitric oxide response to endotoxin. *Ann Surg.* 251: 120-126.

29. Cui, W., D. D. Taub, and K. Gardner. 2007. qPrimerDepot: a primer database for quantitative real time PCR. *Nucleic Acids Res.* 35 (Database issue): D805-809.

30. Rodrigues, J. C., G. C. Gonzalez, L. Zhang, G. Ibrahim, .1. J. Kelly, M. P. Gustafson, Y. Lin, A. B. Dietz, P. A. Forsyth, V. W. Yong, and I. F. Parney. 2009. Normal human monocytes exposed to glioma cells acquire myeloid-derived suppressor cell-like properties. *Neuro Oncol.* 4: 351-365.

31. Dong, R., S. Adams, G. Bouma, A. Eddaouda, P. Chana, D. Moulding, A. Duncan, and J. Anderson. 2010. Newly identified multinuclear cells in cultured human dendritic cells possess the phenotype of regulatory DC. Keystone Symposium Molecular and Cellular Biology and Immune Escape in Cancer, Keystone, Colo., Feb. 7-12, 2010; p. 171, abstract 135.

32. de Kleer, I., Y. Vercoulen, M. Klein, J. Meerding, S. Albani, R. van der Zee, B. Sawitzki, A. Hamann, W. Kuis, and B. Prakken. 2010. CD30 discriminates heat shock protein 60-induced FOXP3+ CD4+ T cells with a regulatory phenotype. *J Immunol.* 185: 2071-2079.

33. del Rio, M. L., G. Bernhardt, J. I. Rodriguez-Barbosa, and R. Förster R. 2010. Development and functional specialization of CD103$^+$ dendritic cells. *Immunol Rev.* 234: 268-281.

34. Hori, S., T. Nomura, and S. Sakaguchi. 2003. Control of regulatory T cell development by the transcription factor Foxp3. *Science.* 299: 1057-1061.

35. Corzo, C. A., T. Condamine, L. Lu, M. J. Cotter, J. I. Youn, P. Cheng, H. I. Cho, E. Celis, D. G. Quiceno, T. Padhya, T. V. McCaffrey, J. C. McCaffrey, and D. f. Gabrilovich. 2010. HIF-1α regulates function and differentiation of myeloid-derived suppressor cells in the tumor microenvironment. *J Exp Med.* 207: 2439-2453.

36. Ramji, D. P., and P. Foka. 2002. CCAAT/enhancer-binding proteins: structure, function and regulation. *Biochem J.* 365 (Pt 3): 561-575.

37. Bronte, V. 2010. The transcription factor C/EBPb is a master regulator of tumor-induced, myeloid-dependent immune suppression. In *Molecular and Cellular Biology and Immune Escape in Cancer*, February 7-12. Keystone Symposia on Molecular and Cellular Biology, Silverthorne, Colo. p. 182.

38. Ko, J. S., P. Rayman, J. Ireland, S. Swaidani, G. Li, K. D. Bunting, B. Rini, J. H. Finke, and P. A. Cohen. 2010. Direct and differential suppression of myeloid-derived suppressor cell subsets by sunitinib is compartmentally constrained. *Cancer Res.* 70: 3526-3536.

39. Corzo, C. A., M. J. Cotter, P. Cheng, F. Cheng, S. Kusmartsev, E. Sotomayor, T. Padhya, T. V. McCaffrey, J. C. McCaffrey, and D. I. Gabrilovich. 2009. Mechanism regulating reactive oxygen species in tumor-induced myeloid-derived suppressor cells. *J Immunol.* 182: 5693-5701.

40. Sica, G. L., I. H. Choi, G. Zhu, K. Tamada, S. D. Wang, H. Tamura, A. I. Chapoval, D. B. Flies, J. Bajorath, and L. Chen. 2003. B7-H4, a molecule of the B7 family, negatively regulates T cell immunity. *Immunity.* 18: 849-861.

41. Sadun, R. E., S. M. Sachsman, X. Chen, K. W. Christenson, W. Z. Morris, P. Hu, and A. L. Epstein. 2007. Immune signatures of murine and human cancers reveal unique mechanisms of tumor escape and new targets for cancer immunotherapy. *Clin Cancer Res.* 13: 4016-4025.

42. Jung, Y. J., J. S. Isaacs, S. Lee, J. Trepel, and L. Neckers. 2003. IL-1 beta-mediated up-regulation of HIF-1alpha via an NFkappaB/COX-2 pathway identifies HIF-1 as a critical link between inflammation and oncogenesis. *FASEB J.* 17: 2115-2117.

43. Xu, Q., J. Briggs, S. Park, G. Niu, M. Kortylewski, S. Zhang, T. Gritsko, J. Turkson, H. Kay, G. L. Semenza, J. Q. Cheng, R. Jove, and H. Yu. 2005. Targeting Stat3 blocks both HIF-1 and VEGF expression induced by multiple oncogenic growth signaling pathways. *Oncogene.* 24: 5552-5560.

44. Ramadori, P., G. Ahmad, and G. Ramadori. 2010. Cellular and molecular mechanisms regulating the hepatic erythropoietin expression during acute-phase response: a role for IL-6. *Lab Invest.* 90: 1306-1324.

45. Rius, J., M. Guma, C. Schachtrup, K. Akassoglou, A. S. Zinkernagel, V. Nizet, R. S. Johnson, G. G. Haddad, and M. Karin. 2008. NF-kappaB links innate immunity to the hypoxic response through transcriptional regulation of HIF-1alpha. *Nature.* 453: 807-811.

46. Watson, J. A., C. J. Watson, A. M. McCrohan, K. Woodfine, M. Tosetto, J. McDaid, E. Gallagher, D. Betts, J. Baugh, J. O'Sullivan, A. Murrell, R. W. Watson, and A. McCann. 2009. Generation of an epigenetic signature by chronic hypoxia in prostate cells. *Hum Mol Genet.* 18: 3594-3604.

47. Peyssonnaux, C., P. Cejudo-Martin, A. Doedens, A. S. Zinkernagel, R. S. Johnson, and V. Nizet. 2007. Cutting edge: Essential role of hypoxia inducible factor-1alpha in development of lipopolysaccharide-induced sepsis. *J Immunol.* 178: 7516-7519.

---

What is claimed is:

1. A method for generating human myeloid-derived suppressor cells (MDSC) from a source of myeloid lineage cells, wherein said induced MDSC have a phenotype selected from the group consisting of CD33$^+$CD11b$^-$ and CD33$^-$CD11b$^+$, comprising:
   (a) contacting the source of myeloid lineage cells with a tumor sample under conditions sufficient to induce MDSC;
      wherein the tumor sample for CD33$^+$CD11b$^-$ is isolated from a cancer type selected from the group of thyroid, brain, melanoma, cervical/endometrial, ovarian, bladder, non-small cell lung cancer, small cell lung cancer, liver, renal, prostate, gastric, colorectal, pancreatic,
      wherein the tumor sample for CD33$^-$CD11b$^+$ is isolated from a cancer type selected from breast, non-small cell lung cancer and glioma; and,
   (b) isolating the induced MDSC.

2. The method according claim 1, wherein the source of myeloid lineage cells is selected from the group consisting of blood, tumor, lymph, lymph node tissue, spleen cells, cerebrospinal fluid, ascities, and pleural effusions.

3. The method according to claim 2, wherein the source of myeloid lineage cells is peripheral blood mononuclear cells.

4. The method according to claim 1, wherein the source of myeloid lineage cells is from a healthy donor.

5. A method for generating human induced myeloid-derived suppressor cells (MDSC) from a source of myeloid lineage cells, wherein said induced MDSC have a phenotype selected from the group consisting of CD11$^-$CD33$^+$HIF1α$^+$/STAT3$^+$ and CD33$^-$CD11b$^+$/EBPβ$^+$ comprising:
   (a) contacting the source of myeloid lineage cells with a tumor sample under conditions sufficient to induce MDSC, wherein the tumor sample for CD33$^+$CD11b$^-$HIF1α$^+$/STAT3$^+$ is isolated from a cancer type selected from the group of thyroid, brain, melanoma, cervical/endometrial, ovarian, bladder, non-small cell lung cancer, small cell lung cancer, liver, renal, prostate, gastric, colorectal, pancreatic,
      wherein the tumor sample for CD33$^-$CD11b$^+$/EBPβ$^+$ is isolated from a cancer type selected from breast, non-small cell lung cancer and glioma; and,
   (b) isolating the induced MDSC.

6. The method according claim 5, wherein the source of myeloid lineage cells is selected from the group consisting of blood, tumor, lymph, lymph node tissue, spleen cells, cerebrospinal fluid, ascities, and pleural effusions.

7. The method according to claim 5, wherein the source of myeloid lineage cells is peripheral blood mononuclear cells.

8. The method according to claim 5, wherein the source of myeloid lineage cells is from a healthy donor.

* * * * *